United States Patent
Kitagawa et al.

(10) Patent No.: US 11,202,849 B2
(45) Date of Patent: Dec. 21, 2021

(54) MEDICAL DEVICE AND METHOD FOR MANUFACTURING THE SAME

(71) Applicant: Toray Industries, Inc., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/631,339

(22) PCT Filed: Aug. 7, 2018

(86) PCT No.: PCT/JP2018/029531
§ 371 (c)(1),
(2) Date: Jan. 15, 2020

(87) PCT Pub. No.: WO2019/031477
PCT Pub. Date: Feb. 14, 2019

(65) Prior Publication Data
US 2020/0215226 A1   Jul. 9, 2020

(30) Foreign Application Priority Data

Aug. 9, 2017 (JP) .............................. JP2017-154001

(51) Int. Cl.
| | | |
|---|---|---|
| A61L 27/16 | (2006.01) | |
| A61L 15/24 | (2006.01) | |
| A61L 15/26 | (2006.01) | |
| A61L 15/60 | (2006.01) | |
| A61L 27/18 | (2006.01) | |
| A61L 27/40 | (2006.01) | |
| A61L 27/52 | (2006.01) | |
| A61L 29/08 | (2006.01) | |
| A61L 29/12 | (2006.01) | |
| A61L 29/14 | (2006.01) | |
| A61L 31/10 | (2006.01) | |
| A61L 31/12 | (2006.01) | |
| A61L 31/14 | (2006.01) | |
| C08L 33/12 | (2006.01) | |
| C08L 83/04 | (2006.01) | |

(52) U.S. Cl.
CPC .............. *A61L 27/16* (2013.01); *A61L 15/24* (2013.01); *A61L 15/26* (2013.01); *A61L 15/60* (2013.01); *A61L 27/18* (2013.01); *A61L 27/40* (2013.01); *A61L 27/52* (2013.01); *A61L 29/08* (2013.01); *A61L 29/12* (2013.01); *A61L 29/145* (2013.01); *A61L 31/10* (2013.01); *A61L 31/12* (2013.01); *A61L 31/14* (2013.01); *C08L 33/12* (2013.01); *C08L 83/04* (2013.01)

(58) Field of Classification Search
CPC .......... A61L 15/24; A61L 15/26; A61L 15/60; A61L 27/18; A61L 27/40; A61L 27/52; A61L 29/08; A61L 29/12; A61L 29/145; A61L 31/10; A61L 31/12; A61L 31/14; A61L 2/16; A61L 29/14; A61L 27/16; C08L 33/12; C08L 83/04; A61F 2/16; G02C 7/04
See application file for complete search history.

(56) References Cited

U.S. PATENT DOCUMENTS

| | | |
|---|---|---|
| 4,168,112 A | 9/1979 | Ellis et al. |
| 6,428,839 B1 | 8/2002 | Künzler et al. |
| 9,052,442 B2 | 6/2015 | Pruitt et al. |
| 10,222,509 B2 | 3/2019 | Kolluru et al. |
| 10,513,628 B2 | 12/2019 | Qui et al. |
| 2004/0114105 A1 | 6/2004 | Shimoyama et al. |
| 2005/0106207 A1 | 5/2005 | Qiu et al. |
| 2008/0085922 A1* | 4/2008 | Raja .................. A61K 31/4535 514/324 |
| 2014/0198294 A1 | 7/2014 | Nakamura et al. |
| 2014/0240660 A1 | 8/2014 | Fujisawa et al. |
| 2014/0285765 A1 | 9/2014 | Fujisawa et al. |
| 2019/0022282 A1 | 1/2019 | Kitagawa |

FOREIGN PATENT DOCUMENTS

| | | |
|---|---|---|
| EP | 1153964 A2 | 11/2001 |
| EP | 3395376 A1 | 10/2018 |
| EP | 3623860 A1 | 3/2020 |
| JP | 54116947 A | 9/1979 |
| JP | 63246718 A | 10/1988 |
| JP | 2002047365 A | 2/2002 |
| JP | 2003171686 A | 6/2003 |
| JP | 2003535626 A | 12/2003 |
| JP | 2004535227 A | 11/2004 |
| JP | 2010508563 A | 3/2010 |
| JP | 2013533517 A | 8/2013 |
| JP | 2014533381 A | 12/2014 |
| JP | 2017023374 A | 2/2017 |
| WO | 2008076528 A1 | 6/2008 |
| WO | 2013024799 A1 | 2/2013 |
| WO | 2013024800 A1 | 2/2013 |
| WO | 2013024856 A1 | 2/2013 |
| WO | 2013024857 A1 | 2/2013 |
| WO | 2017146102 A1 | 8/2017 |
| WO | 2018207644 A1 | 11/2018 |

OTHER PUBLICATIONS

International Search Report and Written Opinion for International Application No. PCT/JP2018/029531, dated Sep. 18, 2018, 10 pages.
Extended European Search Report for European Application No. 18 843 827.9, dated Apr. 6, 2021, 13 pages.

* cited by examiner

*Primary Examiner* — Matthew P Coughlin
*Assistant Examiner* — Thurman Wheeler
(74) *Attorney, Agent, or Firm* — RatnerPrestia

(57) ABSTRACT

To provide a medical device including a substrate and a hydrophilic polymer layer formed on at least a part of the substrate, which satisfies the following conditions (a) to (d): (a) a polymer constituting the hydrophilic polymer layer is a hydrophilic polymer having an acidic group; (b) the hydrophilic polymer layer has a thickness of 1 nm or more and less than 100 nm; (c) a number ratio of basic group/acidic group of the hydrophilic polymer layer is 0.2 or less; and (d) a liquid film retention time at 40 minutes after ultrasonic cleaning in a phosphate buffer solution is 15 seconds or more. The present invention provides a medical device in which a surface of a substrate is hydrophilized, and a method for manufacturing same by a simple method.

16 Claims, No Drawings

MEDICAL DEVICE AND METHOD FOR MANUFACTURING THE SAME

CROSS REFERENCE TO RELATED APPLICATIONS

This is the U.S. National Phase application of PCT/JP2018/029531, filed Aug. 7, 2018, which claims priority to Japanese Patent Application No. 2017-154001, filed Aug. 9, 2017, the disclosures of each of these applications being incorporated herein by reference in their entireties for all purposes.

FIELD OF THE INVENTION

The present invention relates to a medical device having a hydrophilic surface and a method for manufacturing the same.

BACKGROUND OF THE INVENTION

There have hitherto been used devices using soft materials made of resins such as a silicone rubber and hydrogel and devices using hard materials such as metal and glass in various fields. Applications of devices using soft materials include medical devices for introduction into a living body and for covering a surface of a living body, biotechnology devices such as cell culture sheets and scaffold materials for tissue regeneration, and cosmetic devices such as facial packs. Applications of devices using hard materials include electric appliances such as personal computers, mobile phones, displays, etc., ampules for use in injections, and use as diagnostic and analysis tools such as capillaries, biosensing chips, and the like.

When various devices are introduced into a living body as a medical device or attached to a surface of a living body, it becomes important to perform surface modification of a substrate of the medical device for the purpose of improving biocompatibility. If it is possible to impart better properties such as hydrophilicity, lubricity, and biocompatibility than before surface modification to the medical device by surface modification, users (patients, etc.) can expect an improvement in tactile sensation, reduction of discomfort, and the like.

Various methods have been known as a method for modification of a surface of a substrate of medical devices.

In the prior art, since it was difficult to impart sufficient hydrophilicity in the case of one polymer material, there has been known a method of laminating by forming a layer of each of two or more polymer materials one by one through coating (see, for example, Patent Literature 1). Of these, a method of laminating by forming a layer of each of two or more polymer materials one by one on a layer having a charge opposite to that of the lower layer to coat layers having alternately different charges is called a layer by layer method (LbL method) or the like. In such coating obtained by the LbL method, it is considered that each layer of a substrate and a polymer material is bonded to other layer by the electrostatic interaction.

There has also been known a method in which two or more polymer materials are crosslinked to a substrate and a polymer layer having a thickness of 0.1 μm or more is coated on the substrate (see, for example, Patent Literature 2).

To improve cost efficiency, there has recently been disclosed, as an improved method of the LbL method, a method in which a polyionic substance and a hydrolysate substance during autoclaving are used and the polyionic substance is adsorbed onto a surface of a silicone hydrogel by a single heat treatment and, at the same time, the surface of the silicone hydrogel is hydrophilized (see Patent Literature 3).

There is also disclosed a method in which two hydrophilic polymers are crosslinked on a surface of a silicone hydrogel by a single heat treatment (see Patent Literature 4).

There is also disclosed a surface coating of a contact lens with an ionic polymer (see Patent Literatures 5 to 7).

There is also disclosed surface coating of a medical device, which improves the wettability using a wetting agent without adding a coupling agent (see Patent Literature 8).

PATENT LITERATURE

[Patent Literature 1] WO 2013/024799 A
[Patent Literature 2] JP 2013-533517 W
[Patent Literature 3] JP 2010-508563 W
[Patent Literature 4] JP 2014-533381 W
[Patent Literature 5] JP 54-116947 A
[Patent Literature 6] JP 63-246718 A
[Patent Literature 7] JP 2002-047365 A
[Patent Literature 8] JP 2003-535626 W

SUMMARY OF THE INVENTION

However, in conventional LbL coating as mentioned in Patent Literature 1, it is usually performed to laminate multilayers of about 3 to 20 layers. In order to laminate multilayers, many manufacturing processes are required, and thus manufacturing costs may increase. As a result of a study on this LbL coating, a problem was found in durability.

In the coating using crosslinking as mentioned in Patent Literature 2, since a crosslinked polymer layer has a thickness of 0.1 μm or more, for example, in the case of using for a medical device such as an ophthalmic lens, if the lens is not strictly controlled, there is a problem that light refraction for focusing on the retina is easily disturbed thus causing poor visibility. Since there is a need to strictly control the thickness of the polymer layer and there is a need for a complicated process for crosslinking the polymer to the substrate, manufacturing costs may increase.

In the improved LbL coating as mentioned in Patent Literature 3, applicable substrate is limited to a hydrous hydrogel. As a result of further study on the improved LbL coating, performances such as surface hydrophilicity were insufficient.

With respect to the method in which two hydrophilic polymers are crosslinked by a single heat treatment as mentioned in Patent Literature 4, applicable substrate is also limited to a hydrous hydrogel. In the method as mentioned in Patent Literature 4, there is a need for a process in which a carboxyl group-containing polymer is crosslinked to a silicone hydrogel surface before a heat treatment. Via a covalent bond between an epoxy group of a crosslinkable hydrophilic polymer material and a carboxyl group crosslinked on the silicone hydrogel surface, a hydrophilic polymer is crosslinked on a lens surface. This crosslinking is performed in an aqueous solution. Since there is a need for such a complicated process, manufacturing costs may increase.

In surface coating of a contact lens with an ionic polymer as mentioned in Patent Literatures 5 to 7, performances such as surface hydrophilicity were still insufficient.

In surface coating of a medical device as mentioned in Patent Literature 8, performances such as surface hydrophilicity were still insufficient.

The present invention has been made in view of aforementioned problems of prior art. Thus, it is an object of the present invention to provide a medical device whose surface is hydrophilized, excellent in durability and a method for simply producing the same.

To achieve the above object, the present invention according to exemplary embodiments has the following structures.

The present invention in an embodiment is directed to a medical device including a substrate and a hydrophilic polymer layer formed on at least a part of the substrate, which satisfies the following conditions (a) to (d):
(a) a polymer constituting the hydrophilic polymer layer is a hydrophilic polymer having an acidic group;
(b) the hydrophilic polymer layer has a thickness of 1 nm or more and less than 100 nm;
(c) a number ratio of basic group/acidic group of the hydrophilic polymer layer is 0.2 or less; and
(d) a liquid film retention time at 40 minutes after ultrasonic cleaning in a phosphate buffer solution is 15 seconds or more.

The present invention in an embodiment is also directed to a method for manufacturing a medical device, the method including: a step of disposing the substrate in a solution having an initial pH of 2.0 or higher and 6.0 or lower and heating the solution, wherein the solution contains the hydrophilic polymer and an acid.

According to embodiments of the present invention, unlike the prior art, it is possible to obtain a medical device imparted with hydrophilicity on a surface, excellent in durability. Applicable substrate is not limited to a hydrous hydrogel and a silicone hydrogel. These medical devices can be obtained by a simple method.

DETAILED DESCRIPTION OF EMBODIMENTS OF THE INVENTION

The present invention in an embodiment relates to a medical device including a substrate and a hydrophilic polymer layer formed on at least a part of the substrate, which satisfies the following conditions (a) to (d):
(a) a polymer constituting the hydrophilic polymer layer is a hydrophilic polymer having an acidic group;
(b) the hydrophilic polymer layer has a thickness of 1 nm or more and less than 100 nm;
(c) a number ratio of basic group/acidic group of the hydrophilic polymer layer is 0.2 or less; and
(d) a liquid film retention time at 40 minutes after ultrasonic cleaning in a phosphate buffer solution is 15 seconds or more.

The medical device of the present invention may have a lens shape and is preferably an ophthalmic lens. Specific examples thereof include ophthalmic lenses such as contact lens, intraocular lens, artificial cornea, corneal inlay, corneal onlay, and eyeglass lens. Among ophthalmic lenses, contact lens is one of the most preferred embodiments of the present invention.

The medical device of the present invention may be in the form of a tube. Examples of a tubular device include an infusion tube, a gas delivery tube, a drainage tube, a blood circuit, a coating tube, a catheter, a stent, a sheath, a tube connector, an access port, and the like.

The medical device of the present invention may be in the form of a sheet or a film. Specific examples thereof include a dermal covering material, a wound dressing material, a skin protection material, a skin medicine carrier, a biosensor chip, an endoscopic dressing material, and the like.

The medical device of the present invention may have a storage container shape. Specific examples thereof include a drug carrier, a cuff, a drainage bag, and the like.

An ophthalmic lens, especially a contact lens, is one of most preferred embodiments of the present invention.

In an embodiment of the present invention, it is possible to use, as a substrate of the medical device, both a hydrous substrate and a non-hydrous substrate. Examples of the material of the hydrous substrate include a hydrogel and a silicone hydrogel. The silicone hydrogel is particularly preferable because of having flexibility which imparts excellent comfort, and high oxygen permeability. Examples of the non-hydrous substrate include a low water content soft material and a low water content hard material.

The present invention according to an embodiment is also applicable to an ordinary hydrogel containing no silicone and a hydrogel containing silicone (hereinafter also referred to as silicone hydrogel) with respect to the material of the hydrous substrate. It is possible to use particularly suitably for the silicone hydrogel since surface physical properties can be significantly improved.

Hereinafter, United States Adopted Names (USAN) may be used to represent the material. In the USAN, there are cases where variations of the material are expressed by adding symbols such as A, B, and C at the end. However, in the present specification, all variations are expressed when no symbol is added at the end. For example, when simply written as "ocufilcon", it expresses all variations of "ocufilcon A", "ocufilcon B", "ocufilcon C", "ocufilcon D", "ocufilcon E", "ocufilcon F", and the like.

For example, when a hydrogel is a contact lens, specific example of the hydrogel is preferably a hydrogel selected from the group belonging to contact lens classification Group 1 to Group 4 defined by Food and Drug Administration (FDA). Group 2 and Group 4 are more preferable, and Group 4 is particularly preferable because of exhibiting satisfactory water wettability and antifouling properties.

Group 1 represents a nonionic hydrogel lens having a moisture content of less than 50% by mass. Specific examples thereof include tefilcon, tetrafilcon, helfilcon, mafilcon, polymacon, and hioxifilcon.

Group 2 represents a nonionic hydrogel lens having a moisture content of 50% by mass or more. Specific examples thereof include alfafilcon, omafilcon, hioxifilcon, nelfilcon, nesofilcon, hilafilcon, and acofilcon. Omafilcon, hioxifilcon, nelfilcon, and nesofilcon are more preferable, omafilcon and hioxifilcon are still more preferable, and omafilcon is particularly preferable because of exhibiting satisfactory water wettability and antifouling properties.

Group 3 represents an ionic hydrogel lens having a moisture content of less than 50% by mass. Specific examples thereof include deltafilcon, and the like.

Group 4 represents an ionic hydrogel lens having a moisture content of 50% by mass or more. Specific examples thereof include etafilcon, focofilcon, ocufilcon, phemfilcon, methafilcon, and vilfilcon. Etafilcon, focofilcon, ocufilcon, and phemfilcon are more preferable, etafilcon and ocufilcon are still more preferable, and etafilcon is particularly preferable because of exhibiting satisfactory water wettability and antifouling properties.

For example, when a silicone hydrogel is a contact lens, specific example of the silicone hydrogel is preferably a silicone hydrogel selected from the group belonging to contact lens classification Group 5 defined by Food and Drug Administration (FDA).

The silicone hydrogel is preferably a polymer which has a silicon atom in the main chain and/or side chain and has hydrophilicity, and examples thereof include a copolymer of a monomer having a siloxane bond and a hydrophilic monomer.

Specific examples thereof include lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon. Lotrafilcon, galyfilcon, narafilcon, senofilcon, comfilcon, enfilcon, stenfilcon, somofilcon, delefilcon, balafilcon, and samfilcon are more preferable, lotrafilcon, narafilcon, senofilcon, comfilcon, and enfilcon are still more preferable, and narafilcon, senofilcon, and comfilcon are particularly preferable because of exhibiting satisfactory water wettability and antifouling properties.

The low water content soft material and the low water content hard material are preferably a material having a silicon atom because of exhibiting high oxygen permeability capable of supplying sufficient oxygen to the cornea in the case of using, for example, for a medical device such as an ophthalmic lens.

For example, when a low water content hard material is a contact lens, specific example of the low water content hard material is preferably a low water content hard material selected from the group belonging to contact lens classification defined by Food and Drug Administration (FDA).

The low water content hard material is preferably a polymer having a silicon atom in the main chain and/or side chain. For example, it is a molded article composed of a polymer having a siloxane bond as a main component. Among these polymers having a silicon atom, those in which the silicon atom is contained in the polymer by a siloxane bond are preferable from the viewpoint of the oxygen permeability. Specific examples of the polymer include tris(trimethylsilyloxy)silyl]propyl methacrylate, polydimethylsiloxane having a double bond at both ends, a homopolymer using silicone-containing (meth) acrylate, or a copolymer of these monomers and other monomers.

Specific examples thereof include neofocon, pasifocon, telefocon, silafocon, paflufocon, petrafocon, and fluorofocon. Neofocon, pasifocon, telefocon, and silafocon are more preferable, neofocon, pasifocon, and telefocon are still more preferable, and neofocon is particularly preferable because of exhibiting satisfactory water wettability and antifouling properties.

When the medical device of the present invention is an embodiment other than the contact lens, examples of those suitable as the low water content hard material include polyethylene, polypropylene, polysulfone, polyetherimide, polystyrene, polymethyl methacrylate, polyamide, polyester, epoxy resin, polyurethane, polyvinyl chloride, and the like. Polysulfone, polystyrene, and polymethyl methacrylate are still more preferable, and polymethyl methacrylate is particularly preferable because of exhibiting satisfactory water wettability and antifouling properties.

Specific examples of the low water content soft material include low water content soft materials used in medical devices as mentioned in WO 2013/024799 A in which a moisture content is 10% by mass or less, an elastic modulus is 100 kPa or more and 2,000 kPa or less, and a tensile elongation is 50% or more and 3,000% or less. Elastofilcon is also suitable.

When the medical device of the present invention is an embodiment other than an ophthalmic lens, suitable examples of the low water content soft material include silicone elastomer, soft polyurethane, polyvinyl acetate, ethylene-vinyl acetate copolymer, soft polyester resin, soft acrylic resin, soft polyvinyl chloride, natural rubber, various synthetic rubbers, and the like.

According to an embodiment of the present invention, it is possible to impart moderate hydrophilicity and lubricity to a surface of the medical device even if the substrate may be hydrous or low hydrous. Therefore, the moisture content of substrate may be 0 to 99% by mass. The moisture content of the substrate is preferably 0.0001% by mass or more, and particularly preferably 0.001% by mass or more, since the effect of imparting moderate hydrophilicity and lubricity to the surface of the medical device is further enhanced. The moisture content of the substrate is preferably 60% by mass or less, more preferably 50% by mass or less, and still more preferably 40% by mass or less.

When the medical device is a contact lens, since it is easy to ensure the movement of the lens in eyes, the moisture content of the substrate is preferably 15% by mass or more, and sill more preferably 20% by mass or more.

According to an embodiment of the present invention, by including a hydrophilic polymer layer on at least a part of the substrate, the hydrophilicity is imparted to at least a part of the medical device. The expression that the substrate includes a hydrophilic polymer layer means that the hydrophilic polymer is formed as a layer on the substrate surface. A part of the hydrophilic gel layer may enter into the inside of the substrate.

The material constituting the hydrophilic polymer layer is usually a material different from that of the substrate. However, as long as a predetermined effect can be obtained, the material may be the same material as that constituting the substrate.

The polymer formed on the hydrophilic polymer layer is composed of a material having hydrophilicity. As long as the development of the hydrophilicity is not impaired, additives other than the material may be included. Here, the material having the hydrophilicity is a material which is soluble in 100 parts by mass of water at room temperature (20 to 23° C.) in the amount of 0.0001 part by mass or more, preferably 0.01 part by mass or more, more preferably 0.1 part by mass or more, and particularly preferably 1 part by mass or more, based on 100 parts by mass of water.

As the polymer forming the hydrophilic polymer layer, a hydrophilic polymer having an acidic group is used. The hydrophilic polymer having an acidic group is preferable because it can form a surface excellent in not only water wettability but also antifouling properties against body fluid, and the like. The acidic group as used herein is preferably, for example, a group selected from a carboxy group and a sulfonic acid group, and particularly preferably a carboxy group. The carboxy group or the sulfonic acid group may be in the form of a salt.

Examples of the hydrophilic polymer having an acidic group include polymethacrylic acid, polyacrylic acid, poly (vinylbenzoic acid), poly(thiophene-3-acetic acid), poly(4-styrenesulfonic acid), polyvinylsulfonic acid, poly(2-acrylamido-2-methylpropanesulfonic acid), and salts thereof. Those mentioned above are examples of a homopolymer, and it is also possible to suitably use a copolymer of hydrophilic monomers constituting the hydrophilic polymer, or a copolymer of the hydrophilic monomer and the other monomer.

When the hydrophilic polymer having an acidic group is a copolymer, the hydrophilic polymer having an acidic group constituting the copolymer is preferably a monomer having a group selected from an allyl group, a vinyl group, and a (meth)acryloyl group in view of high polymerizability, and particularly preferably a monomer having a (meth)

acryloyl group. Suitable examples of such monomer include (meth)acrylic acid, vinylbenzoic acid, styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid and salts thereof is particularly preferable.

It is preferable that the hydrophilic polymer having an acidic group has an amide group, in addition to the acidic group. When having an amide group, in addition to the acidic group, moderate viscosity is exhibited when the hydrophilic polymer is dissolved in water, thus making it possible to form a surface having not only water wettability but also lubricity.

Examples of the hydrophilic polymer having an acidic group and an amide group include polyamides having a carboxyl group, a copolymer of the hydrophilic monomer having an acidic group and a monomer having an amide group, and the like.

Suitable examples of the polyamides having a carboxyl group include polyamino acids such as polyaspartic acid and polyglutamic acid, and polypeptides.

In view of ease of polymerization, the monomer having an amide group is preferably a monomer selected from a monomer having a (meth)acrylamide group and N-vinylcarboxylic acid amide (including cyclic one). Suitable Examples of such monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloyl morpholine, and acrylamide. Of these, N-vinylpyrrolidone, N,N-dimethylacrylamide, and N,N-diethylacrylamide are preferable in view of the lubricity, and N,N-dimethylacrylamide is particularly preferable.

Preferred specific examples of the copolymer of a hydrophilic monomer having an acidic group and a monomer having an amide group include a (meth)acrylic acid/N-vinylpyrrolidone copolymer, a (meth)acrylic acid/N,N-dimethylacrylamide copolymer, a (meth)acrylic acid/N,N-diethylacrylamide copolymer, a 2-acrylamide-2-methylpropanesulfonic acid/N-vinylpyrrolidone copolymer, a 2-acrylamide-2-methylpropanesulfonic acid/N,N-dimethylacrylamide copolymer, and a 2-acrylamide-2-methylpropanesulfonic acid/N,N-diethylacrylamide copolymer. A (meth)acrylic acid/N,N-dimethylacrylamide copolymer is particularly preferable.

When using a copolymer of a hydrophilic monomer having an acidic group and a monomer having an amide group, the copolymerization ratio thereof is preferably in a range of 1/99 to 99/1 in terms of [mass of hydrophilic monomer having an acidic group]/[mass of monomer having an amide group]. The copolymerization ratio of the hydrophilic monomer having an acidic group is more preferably 2% by mass or more, still more preferably 5% by mass or more, yet more preferably 7% by mass or more, and even more preferably 10% by mass or more. The copolymerization ratio of the hydrophilic monomer having an acidic group is more preferably 90% by mass or less, still more preferably 80% by mass or less, and yet more preferably 70% by mass or less. The copolymerization ratio of the monomer having an amide group is more preferably 10% by mass or more, still more preferably 20% by mass or more, and yet more preferably 30% by mass or more. The copolymerization ratio of the monomer having an amide group is more preferably 98% by mass or less, still more preferably 95% by mass or less, yet more preferably 93% by mass or less, and even more preferably 90% by mass or less. When the copolymerization ratios of the hydrophilic monomer having an acidic group and the monomer having an amide group are in the above range, it becomes easy to develop functions such as lubricity and antifouling properties against body fluid.

It is also possible to further copolymerize the hydrophilic monomer having an acidic group and the monomer having an amide group with a monomer having a different acidic group or amide group and a monomer having neither acidic group nor amide group alone or in combination.

Suitable examples of the monomer other than the above monomers include hydroxyethyl (meth)acrylate, hydroxypropyl (meth) acrylate, hydroxybutyl (meth) acrylate, hydroxyethyl(meth)acrylamide, (meth)acrylamide, glycerol (meth)acrylate, caprolactone-modified 2-hydroxyethyl (meth)acrylate, N-(4-hydroxyphenyl)maleimide, hydroxystyrene, and vinyl alcohol (carboxylic acid vinyl ester as a precursor). Of these, in view of ease of polymerization, a monomer having a (meth)acryloyl group is preferable and a (meth)acrylic acid ester monomer is more preferable. Of these, in view of improving antifouling properties against body fluid, hydroxyethyl (meth)acrylate, hydroxypropyl (meth)acrylate, and glycerol (meth)acrylate are preferable, and hydroxyethyl (meth)acrylate is particularly preferable. It is also possible to use a monomer having functions such as hydrophilicity, antibacterial properties, antifouling properties, and medicinal effects.

When a copolymer of a hydrophilic monomer having an acidic group and a monomer having an amide group is copolymerized with a third monomer component which is the monomer having a different acidic group or amide group or the monomer having neither acidic group nor amide group, the copolymerization ratio of the third monomer component is more preferably 2% by mass or more, still more preferably 5% by mass or more, and yet more preferably 10% by mass or more. The copolymerization ratio of the third monomer component is more preferably 90% by mass or less, still more preferably 80% by mass or less, and yet more preferably 70% by mass or less.

If the copolymerization ratios of the monomer having an acidic group, the monomer having an amide group, and the third monomer component are in the above range, functions such as lubricity and antifouling properties against body fluid are easily developed.

As long as properties required to the medical device are not impaired, additives other than the above materials may be included in the hydrophilic polymer layer. In addition to the hydrophilic polymer having an acidic group, one or more other hydrophilic polymers may be included in the hydrophilic polymer layer. Since the manufacturing method may be complicated, it is preferable that the hydrophilic polymer layer is made of only one hydrophilic polymer having an acidic group.

Here, one polymer means a polymer or a polymer group (isomers, complexes, etc.) produced by one synthesis reaction. When a copolymerized polymer is obtained by using plural monomers, even though the constituent monomer species are the same, a polymer synthesized by changing a compounding ratio is not said to be the same one.

The expression that the hydrophilic polymer layer is made of only one hydrophilic polymer having an acidic group means that the hydrophilic polymer layer does not contain any polymer other than the hydrophilic polymer having an acidic group, or even if it contains the other polymer, it means that the content of the other polymer is preferably 3 parts by mass or less based on 100 parts by mass of the hydrophilic polymer having an acidic group. The content of the other polymer is more preferably 0.1 part by mass or less, and still more preferably 0.0001 part by mass or less.

Even if the other polymer is a basic polymer, when the content is in the above range, it is possible to suppress the occurrence of a problem with transparency. In the prior art, an acidic polymer and a basic polymer were used in combination to laminate a hydrophilic polymer on a surface of the substrate utilizing the electrostatic adsorption effect. However, according to the present invention, a hydrophilic polymer layer made of only one polymer can also be formed on a surface of the substrate.

When the hydrophilic polymer layer has a basic group, a number ratio of basic group/acidic group is preferably 0.2 or less. Since a salt derived from a reaction between an acidic group and a basic group is not formed, and the hydrophilic polymer layer is excellent in transparency, the ratio is more preferably 0.1 or less, and still more preferably 0.05 or less. Here, the basic group represents a basic functional group, and examples thereof include an amino group and a salt thereof.

In an embodiment of the present invention, the hydrophilic polymer having an acidic group constituting the hydrophilic polymer layer forms one or more chemical bonds selected from a hydrogen bond, an ionic bond, a van der Waals bond, a hydrophobic bond, or complex formation with at least a part of the surface of the substrate. Here, the hydrophilic polymer layer may be bonded to the substrate through a covalent bond, or rather, the hydrophilic polymer layer preferably has no covalent bond with the substrate since it becomes possible to manufacture by a simple process.

Depending on the application, the hydrophilic polymer layer preferably exists on the entire surface of one surface of the substrate surface in the medical device of the present invention. In the case of a two-dimensional shape in which the substrate has no thickness or, if any, thickness can be neglected, the hydrophilic polymer layer preferably exists on the entire surface of one surface of the substrate surface. More preferably, the hydrophilic polymer layer exits on the entire surface of the substrate.

Since the hydrophilic polymer can be manufactured by a simple process regardless of whether the substrate is hydrous or non-hydrous, it is preferred that a covalent bond does not exist between the hydrophilic polymer and the substrate. The absence of a covalent bond is judged by having no chemically reactive group. Specific examples of the chemically reactive group include, but are not limited to, an azetidinium group, an epoxy group, an isocyanate group, an aziridine group, an azlactone group, and combinations thereof.

The thickness of the hydrophilic polymer layer is 1 nm or more and less than 100 nm when observing a cross section of the device in a dry state using a scanning transmission electron microscope. When the thickness is in the above range, it becomes easy to exhibit functions such as water wettability and lubricity. The thickness is more preferably 5 nm or more, and still more preferably 10 nm or more. The thickness is more preferably 95 nm or less, still more preferably 90 nm or less, and particularly preferably 85 nm or less. When the thickness of the hydrophilic polymer layer is less than 100 nm, the hydrophilic polymer layer is excellent in water wettability and lubricity and, for example, in the case of using for a medical device such as an ophthalmic lens, refraction of light for focusing on the retina is not disturbed and poor visibility becomes hardly occurs.

The thickness of the hydrophilic polymer layer is preferably 1 nm or more and less than 100 nm when observing a cross section of the device in a frozen state (hereinafter referred to as a frozen state) in a hydrous state using a scanning transmission electron microscope since it becomes easy to exhibit functions such as water wettability and lubricity. The thickness is more preferably 5 nm or more, still more preferably 10 nm or more, and particularly preferably 15 nm or more. The thickness is more preferably 95 nm or less, still more preferably 90 nm or less, and particularly preferably 85 nm or less. It is possible to measure the thickness of the hydrophilic polymer layer in a frozen state by scanning transmission electron microscope observation using a cryotransfer holder.

When the thickness of the polymer layer in a frozen state is 100 nm or more, for example, in the case of using for a medical device such as an ophthalmic lens, refraction of light for focusing on the retina is disturbed and poor visibility is likely to occur, unfavorably.

When the medical device of an embodiment of the present invention is used as a contact lens, an average thickness of a hydrophilic polymer layer on a surface in contact with an eyelid side called a front curve surface may be the same as that of a hydrophilic polymer layer on a surface in contact with a cornea side called a base curve surface. However, since excessive movement of the contact lens during wearing is suppressed, leading to an improvement in comfort, and rather, it is preferable that there is a thickness difference of more than 20% between the front curve surface and the base curve surface. The difference in average thickness is a ratio of the larger average thickness to the smaller average thickness of the hydrophilic polymer layer.

When the hydrophilic polymer layer on the front curve surface is thicker, there is an advantage that the water retention of the front curve surface in contact with air is higher and tears are less likely to evaporate, and thus feeling of dryness during wearing is easily suppressed.

When the hydrophilic polymer layer on the base curve surface is thicker, there is an advantage that the base curve surface is more slidable and friction between the cornea and the base curve surface at the time of blinking is reduced, and thus the cornea is not easily damaged.

The average thickness can be measured by the same method as in the measurement of the thickness of the hydrophilic polymer layer in the dry state. While changing four places, the thickness was measured at five places for each field of view, and an average of thicknesses measured at twenty places is regarded as an average thickness.

The hydrophilic polymer layer is preferably in a state of being separated into two or more layers or two or more phases.

Here, the state where the hydrophilic polymer layer is separated into two or more layers means a state where a multi-layer structure of two or more layers is observed in the hydrophilic polymer layer when a cross section of the medical device is observed using a transmission electron microscope. If it is difficult to judge separation of layers only by observation with a transmission electron microscope, separation of layers is judged by analyzing elements and compositions of a cross section of the medical device using means capable of performing elemental analysis and composition analysis, such as scanning transmission electron microscopy and electron energy-loss spectroscopy, energy dispersive X-ray spectroscopy, or time-of-flight secondary ion mass spectrometry.

The state where the hydrophilic polymer layer is separated into two or more phases means a state where a state of phase separation into two or more phases in the hydrophilic polymer layer is observed when a cross section of the medical device is observed using a transmission electron microscope. The case where it is difficult to judge separation of phases only by observation with a transmission electron microscope is the same as mentioned above.

Two or more polymers have conventionally been required so as to form a polymer layer of two or more layers or two or more phases on a substrate surface. However, it has been found in an embodiment of the present invention that it is possible to form a hydrophilic polymer layer separated into two or more layers or two or more phases on a substrate surface even if only one polymer exists.

When the hydrophilic polymer layer has a multilayer structure of two or more layers, the thickness of the hydrophilic polymer layer sufficiently increases, leading to further improvement in satisfactory water wettability and lubricity. In a state where the hydrophilic polymer layer is separated into two or more phases, it becomes easy to distinguish from foreign matters such as dust when a cross section of the medical device is observed using a transmission electron microscope. Therefore, it is easy to confirm formation of the polymer layer on the substrate surface and is efficient for quality inspection.

In the hydrophilic polymer layer, at least a part of the hydrophilic polymer layer preferably exists in a state of being mixed with the substrate. The state where the hydrophilic polymer layer is mixed with the substrate is determined by the fact that elements derived from the substrate are detected in at least a part of the cross-sectional structure of the substrate before and after the formation of the hydrophilic polymer layer and the hydrophilic polymer layer when a cross section of the medical device is observed using observation means capable of performing elemental analysis or composition analysis, such as scanning transmission electron microscopy, electron energy-loss spectroscopy, energy dispersive X-ray spectroscopy, or time-of-flight secondary ion mass spectrometry. By mixing the hydrophilic polymer layer with the substrate, the hydrophilic polymer can be firmly fixed to the substrate.

When at least a part of the hydrophilic polymer layer exists in a state of being mixed with the substrate, it is preferred to observe a two-layer structure of a "layer in which at least a part of hydrophilic polymer layer is mixed with a substrate" (hereinafter referred to as a "mixed layer") and a "layer made of a hydrophilic polymer" (hereinafter referred to as a "single layer"). The thickness of the mixed layer is preferably 3% or more, more preferably 5% or more, and still more preferably 10% or more, based on the total thickness of the mixed layer and the single layer. The thickness of the mixed layer is preferably 98% or less, more preferably 95% or less, still more preferably 90% or less, and particularly preferably 80% or less, based on the total thickness of the mixed layer and the single layer. Too small thickness ratio of the mixed layer leads to insufficient mixing of the hydrophilic polymer with the substrate, unfavorably. Too large thickness ratio of the mixed layer may lead to insufficient development of properties of the hydrophilic polymer, unfavorably.

From the viewpoint of excellent transparency of the medical device, the number of layers or phases is preferably 2 to 3, and more preferably 2. If the medical device has high transparency, for example, when the medical device is used as a skin material, it is easy to visually observe the state of the skin without peeling the medical device from the skin. If the medical device has high transparency, it can be used as an ophthalmic lens or the like.

When the medical device of an embodiment of the present invention is, for example, a medical device which is used by being attached to a surface of a living body or an ophthalmic device such as an ophthalmic lens, the liquid film retention time on the surface of the medical device is preferably long from the viewpoint of preventing from sticking to the skin of users and preventing from sticking to the cornea of wearers.

Here, the liquid film retention time in the present invention is the time period during which a liquid film on the surface of the medical device is retained without being broken when the medical device immersed in a phosphate buffer solution is pulled up from the liquid and kept so that the surface is vertical in the air. The expression that "liquid film breaks" means a state where a phenomenon of repelling water on the surface of the medical device occurs. The liquid film retention time is preferably 15 seconds or more, more preferably 20 seconds or more, and particularly preferably 25 seconds or more.

In the prior art, when the thickness of the hydrophilic polymer layer on the surface is less than 100 nm, even if the medical device has good water wettability, the water wettability extremely deteriorates when subjected to ultrasonic cleaning, and the water wettability once deteriorated might not be recovered even when it is left to stand in water at room temperature for a short time (for example, about 1 hour). Although the details of the mechanism of this phenomenon are unknown, the phenomenon occurred because the hydrophilic polymer layer on the surface is peeled off or eluted by ultrasonic waves, or the composition of the hydrophilic polymer layer surface changes, resulting in enhanced hydrophobicity. Therefore, a medical device whose wettability deteriorates when subjected to ultrasonic cleaning is not preferable because there is a risk that the surface state changes due to external stimulus, resulting in deterioration of the wettability. To the contrary, a medical device whose surface water wettability does not deteriorate even after being subjected to ultrasonic cleaning, or recovers in a short time after deterioration, can be said to be an excellent medical device whose surface state is hardly changed by external stimulus.

When the medical device of an embodiment of the present invention is an ophthalmic device such as an ophthalmic lens, the liquid film retention time on the surface of the medical device after being subjected to ultrasonic cleaning is preferably long from the viewpoint that the medical device is less likely to impart feeling of dryness, thus making it possible to maintain satisfactory comfort for a long time.

The medical device was subjected to ultrasonic cleaning (power consumption of 40 W) in a phosphate buffer solution for 5 seconds, and then the liquid film retention time on the surface of the medical device after being immersed in the phosphate buffer solution at room temperature for 40 minutes was evaluated. When the liquid film retention time on the surface of the medical device after 40 minutes is 15 seconds or more, it means that the surface of the medical device has sufficient water wettability and durability. The liquid film retention time is preferably 15 seconds or more, more preferably 20 seconds or more, and particularly preferably 25 seconds or more. In particular, when the liquid film retention time is equivalent to that before ultrasonic cleaning, it is preferable because more excellent durability is exhibited. Details of the measurement method will be described later.

When the medical device of an embodiment of the present invention is an ophthalmic device such as an ophthalmic lens, the dynamic contact angle of the surface of the medical device is preferably low from the viewpoint of preventing from sticking to the cornea of wearers. The dynamic contact angle is preferably 60° or less, more preferably 55° or less, and particularly preferably 50° or less. The dynamic contact angle (during advancing, immersion rate: 0.1 mm/sec) is measured using a sample wetted with a phosphate buffer solution. Details of the measuring method will be mentioned later.

When the medical device of an embodiment of the present invention is a medical device which is used by being inserted into a living body, a surface of the medical device preferably has excellent lubricity. An indicator representing the lubricity, the friction coefficient measured by the method mentioned in Examples of the present specification is preferably small. The friction coefficient is preferably 0.7 or less, more preferably 0.5 or less, and particularly preferably 0.3 or less. If the friction is extremely small, it may be difficult to handle during wearing, so that the friction coefficient is preferably 0.001 or more, and more preferably 0.002 or more.

The tensile elastic modulus of the medical device of the present invention should be appropriately selected according to the type of the medical device. In the case of a soft medical device such as an ophthalmic lens, the tensile elastic modulus is preferably 10 MPa or less, preferably 5 MPa or less, more preferably 3 MPa or less, still more preferably 2 MPa or less, yet more preferably 1 MPa or less, and most preferably 0.6 MPa or less. The tensile elastic modulus is preferably 0.01 MPa or more, more preferably 0.1 MPa or more, still more preferably 0.2 MPa or more, and most preferably 0.25 MPa or more. In the case of a soft medical device such as an ophthalmic lens, too small tensile elastic modulus may lead to difficulty in handling because of being excessive in softness. Too large tensile elastic modulus may lead to deterioration of comfort because of being excessive in hardness.

The tensile elastic modulus change rate before and after formation of the hydrophilic polymer layer of the medical device of the present invention is preferably 15% or less, more preferably 14% or less, and particularly preferably 13% or less. Too large tensile elastic modulus change rate may lead to deformation and poor tactile sensation, unfavorably. Details of the measuring method will be mentioned later.

The antifouling properties of the device of the present invention can be evaluated by the deposition of mucin and deposition of lipid (methyl palmitate). The smaller the deposition amount by these evaluations, the more tactile sensation is excellent and bacterial propagation risk is reduced, favorably. The mucin deposition amount is preferably 10 µg/cm$^2$ or less, more preferably 8 µg/cm$^2$ or less, and particularly preferably 6 µg/cm$^2$ or less. Details of the measuring method will be mentioned later.

Next, a method for manufacturing a medical device of the present invention will be described.

The method for manufacturing a medical device according to an embodiment of the present invention includes a step of disposing a substrate in a solution having an initial pH of 2.0 or higher and 6.0 or lower and heating the solution, wherein the solution contains the hydrophilic polymer and an acid.

Here, the inventors of the present invention have found that excellent water wettability and lubricity can be imparted to a medical device by an extremely simple method in which a substrate is heated in a state of being disposed in a solution having an initial pH of 2.0 or higher and 6.0 or lower, which contains a hydrophilic polymer and an acid (preferably organic acid). According to this method, a substrate with a hydrophilic polymer layer having an acidic group layer can be obtained without using a conventionally known special method, for example, a method in which the electrostatic adsorption effect using an acidic polymer in combination with a basic polymer is utilized, leading to industrially very important meaning from the viewpoint of shortening the manufacturing process.

The hydrophilic polymer preferably has a molecular weight of 2,000 to 1,500,000. The molecular weight is preferably 50,000 or more, more preferably 250,000 or more, and still more preferably 500,000 or more, because of exhibiting sufficient water wettability and lubricity. The molecular weight is preferably 1,200,000 or less, more preferably 1,000,000 or less, and still more preferably 900,000 or less. Here, a weight average molecular weight in terms of polyethylene glycol measured by a gel permeation chromatography method (aqueous solvent) is used as the molecular weight.

An increase in concentration of the hydrophilic polymer in the solution during manufacture generally leads to an increase in thickness of the thus obtained hydrophilic polymer layer. However, too high concentration of the hydrophilic polymer may lead to an increase in difficulty of handling during manufacture due to an increase in viscosity, so that the concentration in the solution of the hydrophilic polymer is preferably 0.0001 to 30% by mass. The concentration of the hydrophilic polymer is more preferably 0.001% by mass or more, and still more preferably 0.005% by mass or more. The concentration of the hydrophilic polymer is more preferably 20% by mass or less, and still more preferably 15% by mass or less.

In the above process, the initial pH value of the solution containing a hydrophilic polymer is preferably in a range of 2.0 to 6.0 since turbidity does not occur in the solution to obtain a medical device having satisfactory transparency. The initial pH is more preferably 2.1 or higher, still more preferably 2.2 or higher, yet more preferably 2.4 or higher, and particularly preferably 2.5 or higher. The initial pH is more preferably 5.0 or lower, still more preferably 4.0 or lower, and yet more preferably less than 3.5.

If the initial pH is 2.0 or higher, turbidity of the solution is less likely to occur. It is preferred that turbidity does not occur in the solution because the surface of the device may have high water wettability and lubricity. When the initial pH is 6.0 or lower, the thus obtained hydrophilic polymer layer may not be separated into two or more layers or two or more phases, leading to deterioration of water wettability and lubricity of the surface of the medical device, favorably.

Since it is possible to impart excellent water wettability and lubricity to the substrate, when the substrate is a material having a silicon atom, the initial pH of the solution containing a hydrophilic polymer is preferably in a range of 3.4 or lower, more preferably 3.3 or lower, and still more preferably 3.0 or lower. When the substrate is a material having no silicon atom, the initial pH is preferably in a range of 4.0 or lower, more preferably 3.5 or lower, and still more preferably 3.3 or lower.

The pH of the solution can be measured using a pH meter (e.g., pH meter Eutech pH 2700 (Eutech Instruments)). Here, the initial pH of the solution containing a hydrophilic polymer means the pH value of the solution measured after adding all the hydrophilic polymer to the solution, followed by stirring at room temperature (23 to 25° C.) for 2 hours with a rotor to thereby make the solution uniform, and before disposing a substrate in the solution and heating the substrate. In the present invention, the pH value is rounded off to one decimal place.

The pH of the solution can change when a heating operation is performed. The pH of the solution after the heating operation is preferably 2.0 to 6.0. The pH after heating is more preferably 2.1 or higher, still more preferably 2.2 or higher, and particularly preferably 2.3 or higher. The pH after heating is more preferably 5.9 or lower, still more preferably 5.5 or lower, yet more preferably 5.0 or lower, and particularly preferably 4.8 or lower. When the pH of the solution after the heating operation is in the above range, the pH of the solution is maintained at appropriate conditions during the heating process, thus obtaining suitable physical properties of the thus obtained medical device. After modifying the surface of the substrate used for the medical device by performing the heating operation in the present invention, the pH can be adjusted by performing a neutralization treatment or adding water. The pH of the solution after performing the heating operation as used herein is the pH before performing such pH adjustment.

A solvent of the solution containing a hydrophilic polymer is preferably water. The pH of the solution can be adjusted by adding an acid to the solution. It is possible to use, as the acid, an organic acid and an inorganic acid. Preferred specific examples of the organic acid include acetic acid, citric acid, formic acid, ascorbic acid, trifluoromethanesulfonic acid, methanesulfonic acid, propionic acid, butyric acid, glycolic acid, lactic acid, malic acid, and the like. Preferred specific examples of the inorganic acid include nitric acid, sulfuric acid, phosphoric acid, hydrochloric acid, and the like. Of these, an organic acid is preferable, an organic acid having 1 to 20 carbon atoms is more preferable, and an organic acid having 2 to 10 carbon atoms is still more preferable, from the viewpoint of the fact that it is easy to obtain more excellent hydrophilic surface, safety to a living body is high, and it is easy to handle. Of these organic acids, acetic acid, citric acid, formic acid, ascorbic acid, trifluoromethanesulfonic acid, methanesulfonic acid, propionic acid, butyric acid, glycolic acid, lactic acid, and malic acid are preferable, formic acid, malic acid, citric acid, and ascorbic acid are more preferable, and citric acid and ascorbic acid are still more preferable. Of these inorganic acids, sulfuric acid is preferable, from the viewpoint of low volatility, odorless, and easy to handle.

Since it becomes easy to finely adjust the pH, and the substrate is less likely to become turbid when the substrate is a material containing a hydrophobic component, a buffering agent is preferably added to the solution.

It is possible to use, as the buffering agent, a physiologically compatible known buffering agent. Examples are as follows: boric acid, borate (e.g., sodium borate), citric acid, citrates (e.g., potassium citrate), bicarbonate (e.g., sodium bicarbonate), phosphate buffer solution (e.g., $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid)), TES (N-[tris(hydroxymethyl)methyl]-2-aminoethanesulfonic acid), and salts thereof.

The buffering agent is used in the effective amount required to achieve desired pH. Usually, the buffering agent exists in the solution in the amount of 0.001% by mass to 2% by mass, preferably 0.01% by mass to 1% by mass, and more preferably 0.05% by mass to 0.30% by mass. The amount may be in a range of a combination of either the upper limit or the lower limit.

Examples of the heating method include a high-pressure steam sterilization method, irradiation with electromagnetic waves (γ ray, microwave, etc.), a dry heat method, a flame method, and the like. From the viewpoint of the water wettability, lubricity, and shortening of the production process, a high-pressure steam sterilization method is most preferable. An autoclave is preferably used as an apparatus.

The heating temperature is preferably 60° C. to 200° C. from the viewpoint of obtaining a medical device surface exhibiting satisfactory water wettability and lubricity and exerting less influence on the strength of the device itself. The heating temperature is more preferably 80° C. or higher, still more preferably 90° C. or higher, yet more preferably 101° C. or higher, and particularly preferably 110° C. or higher. The heating temperature is more preferably 180° C. or lower, still more preferably 170° C. or lower, and particularly preferably 150° C. or lower.

If the heating time is too short, a medical device surface exhibiting satisfactory water wettability and lubricity is unlikely to be obtained. Meanwhile, if the heating time is too long, an adverse influence may be exerted on the strength of the device itself, the heating time is preferably 5 minutes to 600 minutes. The heating time is more preferably 10 minutes or more, and still more preferably 15 minutes or more. The heating time is more preferably 400 minutes or less, and still more preferably 300 minutes or less.

After the above heat treatment, the device thus obtained may be further subjected to the other treatment. Examples of the other treatment include treatments of methods such as a method in which a similar heat treatment is performed in a solution containing a hydrophilic polymer, a method in which a similar heat treatment is performed by using a solution containing no hydrophilic polymer in place of the solution, a method in which irradiation with radiation is performed, a method of performing a layer by layer treatment (LbL treatment) in coatings of polymer materials each having an opposite charge are alternately formed layer by layer, a method in which a crosslinking treatment with metal ions is performed, a method in which a chemical crosslinking treatment is performed, and the like.

Before the above heat treatment, the substrate may be subjected to a pretreatment. Examples of the pretreatment include a hydrolysis treatment with an acid such as polyacrylic acid, or an alkali such as sodium hydroxide.

However, in light of the idea of the present invention which enables hydrophilization of a substrate surface by a simple method, a treatment is preferably performed as long as the manufacturing process does not become too complicated.

Radiations used for the above irradiation with radiation are preferably various ion beams, electron beams, positron beams, X-rays, γ rays, and neutron rays, more preferably electron beams and γ rays, and most preferably γ rays.

As the above LbL treatment, for example, a treatment using an acidic polymer and a basic polymer as mentioned in WO 2013/024800 A is preferably used.

Metal ions used for the above crosslinking treatment with metal ions are preferably various metal ions, more preferably monovalent and divalent metal ions, and most preferably divalent metal ions. Alternatively, a chelate complex may also be used.

As the above chemical crosslinking treatment, for example, a reaction between an epoxy group and a carboxyl group as mentioned in JP 2014-533381 A and a crosslinking treatment formed between known acidic hydrophilic polymers having a hydroxyl group may be used.

In the above method in which a similar heat treatment is performed by using a solution containing no hydrophilic polymer in place of the solution, the solution containing no hydrophilic polymer is not particularly limited and a buffering agent solution is preferable. The above-mentioned substances can be used as the buffering agent.

The pH of the buffering agent solution is preferably within a physiologically acceptable range of 6.3 to 7.8. The pH of the buffering agent solution is preferably 6.5 or higher, and still more preferably 6.8 or higher. The pH of the buffering agent solution is preferably 7.6 or lower, and more preferably 7.4 or lower.

In the manufacturing method of the present invention, the moisture content change rate between the medical device obtained after completion of the heating step and the substrate before starting the heating step is preferably 10 percentage points or less. Here, the moisture content change rate (percentage points) means a difference between the moisture content (% by mass) of the resulting medical device and the moisture content (% by mass) of the substrate as a raw material of the medical device.

The moisture content change rate of the medical device before and after formation of the hydrophilic polymer layer is preferably 10 percentage points or less, more preferably 8 percentage points or less, and particularly preferably 6 percentage points or less, from the viewpoint of preventing poor visibility or deformation caused by distortion of a refractive index due to an improvement in moisture content when the medical device is used in an ophthalmic device such as an ophthalmic lens. Details of the measuring method will be mentioned later.

The size change rate before and after formation of the hydrophilic polymer layer of the medical device is preferably 5% or less, more preferably 4 or less, and particularly preferably 3% or less, from the viewpoint of preventing corneal injury caused by deformation when used in an ophthalmic device such as an ophthalmic lens. Details of the measuring method will be mentioned later.

EXAMPLES

The present invention will be described more specifically by way of Examples, but the present invention is not limited to these Examples. First, analytical method and evaluation method will be shown.

<Water Wettability (Liquid Film Retention Time)>

A medical device was left to stand in a storage container at room temperature for 24 hours or more. With respect to evaluation of only a commercially available contact lens mentioned in Comparative Examples, the medical device was lightly washed in 50 mL of a phosphate buffer solution in a beaker at room temperature and then left to stand in 50 mL of a fresh phosphate buffer solution for 24 hours or more.

The medical device was pulled up from the phosphate buffer solution in which the medical device was left to stand and immersed, and the time during which the liquid film on the surface was retained in the case of keeping in the air was visually observed, and an average of N=3 was judged according to the following criteria.

A: A liquid film on a surface is retained for 20 seconds or more.

B: A liquid film on a surface disappears after 15 seconds or more and less than 20 seconds.

C: A liquid film on a surface disappears after 5 seconds or more and less than 15 seconds.

D: A liquid film on a surface disappears after 1 second or more and less than 5 seconds.

E: A liquid film on a surface instantly disappears (less than 1 second).

<Water Wettability after 40 Minutes of Ultrasonic Cleaning (Liquid Film Retention Time)>

The medical device was left to stand at room temperature for 24 hours or more in a storage container. In a polymethylpentene beaker (capacity: 100 mL), 50 mL of a fresh phosphate buffer solution was charged, and the medical device was immersed therein. Water was charged in a tank of an ultrasonic cleaner (Model VS-25, manufactured by Velvo-Clear Co., Ltd., power consumption 40 W) until it reaches a height of about 3 cm, and the polymethylpentene beaker containing the phosphate buffer solution and the medical device was placed in the ultrasonic cleaner, and then ultrasonic waves were applied for 5 seconds. Thereafter, the medical device was quickly returned in the storage container and left to stand at room temperature for 40 minutes. Thereafter, the medical device was pulled up from the phosphate buffer solution and the time during which the liquid film on the surface was retained in the case of keeping in the air was visually observed, and an average of N=3 (N means the number of samples) was judged according to the following criteria.

A: A liquid film on a surface is retained for 20 seconds or more.

B: A liquid film on a surface disappears after 15 seconds or more and less than 20 seconds.

C: A liquid film on a surface disappears after 5 seconds or more and less than 15 seconds.

D: A liquid film on a surface disappears after 1 second or more and less than 5 seconds.

E: A liquid film on a surface instantly disappears (less than 1 second).

<Lubricity>

A medical device was left to stand in a storage container at room temperature for 24 hours or more. With respect to evaluation of only a commercially available contact lens mentioned in Comparative Examples, the medical device was lightly washed in 50 mL of a phosphate buffer solution in a beaker at room temperature and then left to stand in 50 mL of a fresh phosphate buffer solution for 24 hours or more.

The medical device was pulled up from the phosphate buffer solution in which the medical device was left to stand and immersed, and subjected to sensory evaluation when rubbing with a human finger five times (N=1).

A: There is extremely excellent lubricity (finger slides to flow on a medical device surface and feel no resistance).

B: There is lubricity intermediate between A and C.

C: There is moderate lubricity (finger slides on a medical device surface and hardly feels resistance).

D: Almost no lubricity (intermediate between C and E).

E: No lubricity (finger does not easily slide on a medical device surface and feel large resistance).

<Moisture Content of Substrate and Medical Device>

A substrate was immersed in a phosphate buffer solution and left to stand at room temperature for 24 hours or more. The substrate was pulled out from the phosphate buffer solution and, after wiping off the surface moisture with a wiping cloth ("Kimwipes" (registered trademark) manufactured by NIPPON PAPER CRECIA CO., LTD.), the mass (Ww) of the substrate was measured. Thereafter, the substrate was dried at 40° C. for 2 hours in a vacuum dryer and the mass (Wd) was measured. From these masses, the moisture content of the substrate was calculated by the following formula (1). The case where the obtained value was less than 1% was judged as below the measurement limit, and the column in the table was filled with "less than 1%". An average of N=3 was regarded as the moisture content. The moisture content of the substrate with a hydrophilic polymer layer, i.e., the medical device was also calculated in the same manner.

$$\text{Moisture content (\%) of substrate} = 100 \times (Ww - Wd)/Ww \quad \text{Formula (1)}.$$

<Moisture Content Change Rate between Before and After Formation of Hydrophilic Polymer Layer>

From the measurement results of the moisture content of the substrate and the medical device, the moisture content change rate was calculated by the following formula (2).

$$\text{Moisture content change rate (percentage points)}$$
$$\text{before and after formation of hydrophilic polymer layer} = \text{moisture content (\% by mass) of medical device} - \text{moisture content (\% by mass) of substrate} \quad \text{Formula (2)}$$

<Contact Angle>

Using, as a sample, a strip-shaped test piece measuring about 5 mm×10 mm×0.1 mm cut out from a sample having a contact lens shape, a dynamic contact angle during advancing to a phosphate buffer solution was measured using a wettability test machine WET-6200 (manufactured by RHESCA CO., LTD.). An immersion rate was 0.1 mm/sec, and an immersion depth was 7 mm.

<Friction Coefficient>

The friction coefficient of the medical device surface wetted with a phosphate buffer solution (preservation solution in a package in the case of measuring a commercially available contact lens) was measured with N=5 and an average was regarded as the friction coefficient.

Apparatus: Friction tester KES-SE (manufactured by Kato Tech Co., Ltd.)
Friction SENS: H
Measurement SPEED: 2×1 mm/sec
Friction load: 44 g <Lipid Deposition Amount>

In a 20 cc screw tube, 0.03 g of methyl palmitate, 10 g of pure water, and 1 sample having a contact lens shape were placed. The screw tube was shaken for 3 hours under the conditions at 37° C. and 165 rpm. After shaking, the sample in the screw tube was scrubbed with tap water at 40° C. and a household liquid detergent ("Mama Lemon (registered trademark)" manufactured by Lion Corporation). The washed sample was placed in a screw tube containing a phosphate buffer solution and stored in a refrigerator at 4° C. for 1 hour. Thereafter, the sample was visually observed, and if the turbid portion exists, it was judged that methyl palmitate is deposited and the area of the portion in which methyl palmitate is deposited to the entire surface of the sample was observed.

<Mucin Deposition Amount>

A test piece having a width (minimum portion) of 5 mm and a length of 14 mm was cut out from a sample having a contact lens shape using a prescribed punching die. Mucin Bovine Submaxillary Gland (Catalog No. 499643) available from CALBIOCHEM was used as mucin. The test piece was immersed in an aqueous mucin solution having a concentration of 0.1% under the conditions for 20 hours at 37° C., and then the amount of mucin deposited to the sample was determined by the bicinchoninic acid (BCA) protein assay method. An average of N=3 was regarded as the mucin deposition amount.

<Tensile Elastic Modulus>

A test piece having a width (minimum part) of 5 mm and a length of 14 mm was cut out from a substrate having a contact lens shape using a prescribed punching die. Using the test piece, a tensile test was performed using Tensilon Model RTG-1210 manufactured by A&D Company, Limited. A pulling rate was 100 ram/min and a distance between grips (initial) was 5 mm. Measurements were made on both a substrate before formation of a hydrophilic polymer layer and a medical device after formation of a hydrophilic polymer layer. Measurement was made with N=8 and an average of N=6 excluding the maximum value and the minimum value was regarded as the tensile elastic modulus. The tensile elastic modulus of the substrate with a hydrophilic polymer layer, i.e., the medical device was also measured in the same manner.

<Tensile Elastic Modulus Change Rate Before and After Formation of Hydrophilic Polymer Layer>

From the measurement results of the tensile elastic modulus of the substrate and the medical device, calculation was performed by the following formula (3). An average of N=6 was regarded as the tensile elastic modulus change rate before and after the formation of the hydrophilic polymer layer.

$$\text{Tensile elastic modulus change rate (\%) before and after formation of hydrophilic polymer layer} = \text{(tensile elastic modulus of medical device after formation of hydrophilic polymer layer} - \text{tensile elastic modulus of substrate before formation of hydrophilic polymer layer)/tensile elastic modulus of substrate before formation of hydrophilic polymer layer} \times 100 \quad \text{Formula (3)}.$$

<Size>

The diameter of a substrate having a contact lens shape (N=3) was measured and an average was regarded as the size. The size of the substrate with a hydrophilic polymer layer, i.e., the medical device was also measured in the same manner.

<Size Change Rate Before and After Formation of Hydrophilic Polymer Layer>

From the measurement results of the size of the substrate and the medical device, calculation was performed by the following formula (4). An average of N=3 was regarded as the size change rate before and after the formation of a hydrophilic polymer layer.

$$\text{Size change rate (\%) before and after formation of hydrophilic polymer layer} = \text{(size of device after formation of hydrophilic polymer layer} - \text{size of substrate before formation of hydrophilic polymer layer)/size of substrate before formation of hydrophilic polymer layer} \times 100 \quad \text{Formula (4)}.$$

<Molecular Weight Measurement>

The molecular weight of a hydrophilic polymer was measured under the following conditions.

Apparatus: Prominence GPC system manufactured by Shimadzu Corporation
Pump: LC-20AD
Autosampler: SIL-20AHT
Column oven: CTO-20A
Detector: RID-10A
Column: GMPWXL manufactured by Tosoh Corporation (7.8 mm in inner diameter×30 cm, particle diameter of 13 μm)
Solvent: water/methanol=1/1 (0.1 N lithium nitrate is added)
Flow rate: 0.5 mL/minute
Measurement time: 30 minutes Sample concentration: 0.1 to 0.3% by mass
Sample injection amount: 100 μL
Standard sample: Polyethylene oxide standard sample manufactured by Agilent Technologies, Inc. (0.1 kD to 1258 kD)

<pH Measurement Method>

The pH of the solution was measured using a pH meter Eutech pH 2700 (manufactured by Eutech Instruments Pte Ltd). In the table, the initial pH of a solution containing a hydrophilic polymer was determined by adding all the hydrophilic polymer to the solution mentioned in each Example, followed by stirring at room temperature (23 to 25° C.) for 2 hours with a rotor to thereby make the solution uniform. In the table, "pH after heat treatment" is the pH measured immediately after the solution was cooled to room temperature (23 to 25° C.) after a heat treatment was performed once.

<Judgment of Separation of Hydrophilic Polymer Layer>

Judgment was made whether or not a hydrophilic polymer layer was separated into two or more layers by observing a cross section of a medical device using a transmission electron microscope.
Apparatus: Transmission electron microscope
Condition: Accelerating voltage of 100 kV
Sample preparation: Sample was prepared by a method of staining ultrathin section with $RuO_4$. When it is difficult to discriminate between a substrate and a hydrophilic polymer layer, the sample may be stained with $OsO_4$. In this Example, when the substrate is a silicone hydrogel-based or silicone-based substrate, the sample was stained with $RuO_4$. An ultramicrotome was used to fabricate ultrathin section.

<Elemental Composition Analysis of Hydrophilic Polymer Layer>

Elemental composition analysis of a hydrophilic polymer layer was performed by analyzing a cross section of a medical device frozen in a hydrous state using a cryo-transfer holder using a scanning transmission electron microscope and electron energy loss spectroscopy.
Apparatus: Field emission electron microscope
Acceleration voltage: 200 kV
Measurement temperature: about −100° C.
Electron energy-loss spectroscopy: GATAN GIF Tridiem
Image acquisition: Digital Micrograph
Sample preparation: Sample was prepared by a method of staining ultrathin section with $RuO_4$. When it is difficult to discriminate between a substrate and a coat layer, the sample may be stained with $OsO_4$. In this Example, when the substrate is a silicone hydrogel-based or silicone-based substrate, the sample was stained with $RuO_4$. An ultramicrotome was used to fabricate ultrathin section.

<Thickness of Hydrophilic Polymer Layer>

The thickness of a hydrophilic polymer layer in a dry state was measured by observing a cross section of a medical device in a dry state using a transmission electron microscope. Measurement was made under the conditions mentioned in aforementioned <Judgment of Separation of Hydrophilic Polymer Layer>. While changing four places, the thickness was measured at five places for each field of view, and an average of the thickness at twenty places in total was mentioned.

The thickness of a hydrophilic polymer layer in a frozen state was obtained by observing a cross section of the medical device frozen in a water-containing state using a cryotransfer holder using a scanning transmission electron microscope. Measurement was made under the conditions mentioned in aforementioned <Elemental Composition Analysis of Hydrophilic Polymer Layer>. While changing four places, the thickness was measured at five places for each field of view, and the thickness was measured at twenty places in total. The minimum value and the maximum value of the measured thickness are mentioned.

<Difference in Average Thickness of Hydrophilic Polymer Layer>

The average thickness of a hydrophilic polymer layer was measured under the conditions mentioned in the measurement of the thickness of the hydrophilic polymer layer in a dry state in <Thickness of Hydrophilic Polymer Layer>. The difference in average thickness was calculated by the following formula (5) as a ratio of the larger average thickness to the smaller average thickness of each of the front curves surface and the base curves surface.

Difference in average thickness (%)=(average thickness of a surface having a large average thickness−average thickness of a surface having a small average thickness)/average thickness of a surface having a small average thickness×100   Formula (5).

Reference Example 1

After preparing 28 parts by mass of a polydimethylsiloxane having a methacryloyl group at both ends represented by the formula (M1) (FM 7726, JNC Corporation, Mw: 30,000), 7 parts by mass of a silicone monomer represented by the formula (M2) (FM 0721, JNC Corporation, Mw: 5,000), 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 part by mass of dimethylaminoethyl acrylate (Kohjin Co., Ltd.), preparing 5,000 ppm of a photoinitiator "IRGACURE" (registered trademark) 819 (NAGASE & CO., LTD.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed, followed by stirring. The mixture thus obtained by stirring was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 mW/cm², for 30 minutes) to obtain a molded body made of a low water content soft material having a silicon atom.

After the polymerization, the molded body thus obtained was immersed in an aqueous 100% by mass isopropyl alcohol solution at 60° C. for 1.5 hours together with the mold from which a front curve and a base curve were released, and then a molded body having a contact lens shape was removed from the mold. The molded body thus obtained was immersed in a large excess amount of an aqueous 100% by mass isopropyl alcohol solution maintained at 60° C. for 2 hours to extract impurities such as residual monomers. Thereafter, the molded body was dried at room temperature (23° C.) for 12 hours.

[Chemical Formula 1]

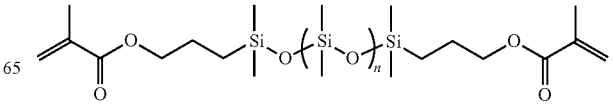

(M1)

-continued

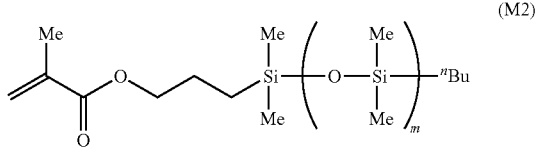

[Phosphate Buffer Solution]

Each composition of the phosphate buffer solutions used in the processes of the following Examples and Comparative Examples and the above-mentioned measurements is as follows.
KCl: 0.2 g/L
$KH_2PO_4$: 0.2 g/L
NaCl: 8.0 g/L
$Na_2HPO_4$ (anhydrous): 1.15 g/L
EDTA: 0.25 g/L Example 1

The molded body obtained in Reference Example 1 was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in pure water was adjusted to pH 2.6 with sulfuric acid. The substrate was immersed in the solution, followed by heating in an autoclave at 121° C. for 30 minutes. The molded body thus obtained was washed with a phosphate buffer solution for 30 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 2

The molded body obtained in Reference Example 1 was used as a substrate. A solution containing 0.2% by mass of an acrylic acid/N,N-dimethylacrylamide copolymer (number ratio of basic group/acidic group: 0, molar ratio in copolymerization: 1/9, Mw: 700,000, manufactured by Osaka Organic Chemical Industry Ltd.) in a phosphate buffer solution was adjusted to pH 2.7 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 3

The molded body obtained in Reference Example 1 was used as a substrate. A solution containing 0.03% by mass of an acrylic acid/N,N-dimethylacrylamide copolymer (number ratio of basic group/acidic group: 0, molar ratio in copolymerization: 1/2, Mw: 500,000, manufactured by Osaka Organic Chemical Industry Ltd.) in a phosphate buffer solution was adjusted to pH 3.1 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 4

The molded body obtained in Reference Example 1 was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 2.4 with sulfuric acid. The substrate was immersed in the solution, followed by heating in an autoclave at 80° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 5

The molded body obtained in Reference Example 1 was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 2.4 with sulfuric acid. The substrate was immersed in the solution, followed by heating in an autoclave at 100° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 6

The molded body obtained in Reference Example 1 was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in pure water was adjusted to pH 2.4 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 7

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 500,000, manufactured by Osaka Organic Chemical Industry Ltd.) in a phosphate buffer solution was adjusted to pH 3.1 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 8

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 500,000, manufactured by Osaka Organic Chemical Industry Ltd.) in a phosphate buffer solution was adjusted to pH 4.1 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 9

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 500,000, manufactured by Osaka Organic Chemical Industry Ltd.) in a phosphate buffer solution was adjusted to pH 5.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 10

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 500,000, manufactured by Osaka Organic Chemical Industry Ltd.) in a phosphate buffer solution was adjusted to pH 5.7 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 11

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.3 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 12

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of an acrylic acid/N,N-dimethylacrylamide copolymer (number ratio of basic group/acidic group: 0, molar ratio in copolymerization: 1/9, Mw: 500,000, manufactured by Osaka Organic Chemical Industry Ltd.) in a phosphate buffer solution was adjusted to pH 3.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 13

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of an acrylic acid/N,N-dimethylacrylamide copolymer (number ratio of basic group/acidic group: 0, molar ratio in copolymerization: 1/2, Mw: 700,000, manufactured by Osaka Organic Chemical Industry Ltd.) in a phosphate buffer solution was adjusted to pH 3.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 14

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 500,000, manufactured by Osaka Organic Chemical Industry Ltd.) in a phosphate buffer solution was adjusted to pH 4.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 15

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.1% by mass of an acrylic acid/vinylpyrrolidone copolymer (number ratio of basic group/acidic group: 0, molar ratio in copolymerization: 1/4, Mw: 800,000, manufactured by Osaka Organic Chemical Industry Ltd.) in a phosphate buffer solution was adjusted to pH 4.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 16

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution containing 0.1% by mass of an acrylic acid/vinylpyrrolidone copolymer (number ratio of basic group/acidic group: 0, molar ratio in copolymerization: 1/9, Mw: 500,000, manufactured by Osaka Organic Chemical Industry Ltd.) in a phosphate buffer solution, which has the pH 4.0 adjusted with sulfuric acid, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 17

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 18

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of an acrylic acid/N,N-dimethylacrylamide copolymer (number ratio of basic group/acidic group: 0, molar ratio in copolymerization: 1/9, Mw: 500,000, manufactured by Osaka Organic Chemical Industry Ltd.) in a phosphate buffer solution was adjusted to pH 3.0 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 19

A commercially available silicone hydrogel lens containing silicone as a main component "MyDay (registered trademark)" (stenfilcon A, manufactured by CooperVision Inc.) was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 2.0 with citric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 20

A commercially available silicone hydrogel lens containing silicone as a main component "MyDay (registered trademark)" (stenfilcon A, manufactured by CooperVision Inc.) was used as a substrate. A solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 2.2 with citric acid. The substrate was immersed in the solution, followed by heating in an autoclave at 90° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

Example 21

A commercially available silicone hydrogel lens containing silicone as a main component "MyDay (registered trademark)" (stenfilcon A, manufactured by CooperVision Inc.) was used as a substrate. A solution containing 0.4% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 2.0 with citric acid. The substrate was immersed in the solution, followed by heating in an autoclave at 90° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 1 to 4.

TABLE 1

|  | Substrate | Moisture content of substrate (%) | Hydrophilic polymer and concentration of solution thereof | Initial pH | pH after heating treatment |
|---|---|---|---|---|---|
| Example 1 | Reference Example 1 | Less than 1% | 0.2% by mass Acrylic acid/N,N-dimethylacrylamide copolymer | 2.6 | 5.0 |
| Example 2 | Reference Example 1 | Less than 1% |  | 2.7 | 4.1 |
| Example 3 | Reference Example 1 | Less than 1% | 0.03% by mass Acrylic acid/N,N-dimethylacrylamide copolymer | 3.1 | 3.8 |
| Example 4 | Reference Example 1 | Less than 1% | 0.2% by mass Acrylic acid/N,N-dimethylacrylamide copolymer | 2.4 | 2.5 |
| Example 5 | Reference Example 1 | Less than 1% |  | 2.4 | 2.7 |
| Example 6 | Reference Example 1 | Less than 1% |  | 2.4 | 3.9 |
| Example 7 | "1-Day Acuvue ®" | 58 | 0.1% by mass Acrylic acid/vinylpyrrolidone copolymer | 3.1 | 3.7 |
| Example 8 | "1-Day Acuvue ®" | 58 |  | 4.1 | 4.9 |
| Example 9 | "1-Day Acuvue ®" | 58 |  | 5.0 | 5.4 |
| Example 10 | "1-Day Acuvue ®" | 58 |  | 5.7 | 5.9 |
| Example 11 | "1-Day Acuvue ®" | 58 | 0.2% by mass Acrylic acid/N,N-dimethylacrylamide copolymer | 3.3 | 5.1 |
| Example 12 | "1-Day Acuvue ®" | 58 |  | 3.0 | 4.7 |
| Example 13 | "1-Day Acuvue ®" | 58 | 0.2% by mass Acrylic acid/N,N-dimethylacrylamide copolymer | 3.0 | 4.8 |
| Example 14 | "1-Day Acuvue ®" | 58 | 0.1% by mass Acrylic acid/vinylpyrrolidone copolymer | 4.0 | 4.7 |
| Example 15 | "1-Day Acuvue ®" | 58 |  | 4.0 | 4.8 |
| Example 16 | "1-Day Acuvue ®" | 58 | 0.1% by mass Acrylic acid/vinylpyrrolidone copolymer | 4.0 | 4.9 |
| Example 17 | "1-Day Acuvue TruEye ®" | 46 | 0.2% by mass Acrylic acid/N,N-dimethylacrylamide copolymer | 3.0 | 4.7 |
| Example 18 | "1-Day Acuvue TruEye ®" | 46 |  | 3.0 | 4.6 |
| Example 19 | "MyDay ®" | 54 | 0.2% by mass Acrylic acid/N,N-dimethylacrylamide copolymer | 2.0 | 2.1 |
| Example 20 | "MyDay ®" | 54 |  | 2.2 | 2.3 |
| Example 21 | "MyDay ®" | 54 |  | 2.0 | 2.0 |

TABLE 2

|  | Liquid film retention time (seconds) | Liquid film retention time at 40 minutes after ultrasonic cleaning (seconds) | Lubricity | Moisture content of medical device (%) | Number of hydrophilic polymer layers | Results of elemental composition analysis of hydrophilic polymer layer | Moisture content change rate of substrate and device (%) | Contact angle (°) | Friction coefficient |
|---|---|---|---|---|---|---|---|---|---|
| Example 1 | A (45 seconds) | A (45 seconds) | A | 3.2 | Two layers | Coating polymer was separated into two layers (one layer of which was mixed with substrate) | 3.2 | 49.3 | 0.003 |
| Example 2 | A (40 seconds) | A (40 seconds) | A | 3.2 | Two layers | Coating polymer was separated into two layers (one layer of which was mixed with substrate) | 3.2 | 51.9 | 0.006 |

TABLE 2-continued

| | Liquid film retention time (seconds) | Liquid film retention time at 40 minutes after ultrasonic cleaning (seconds) | Lubricity | Moisture content of medical device (%) | Number of hydrophilic polymer layers | Results of elemental composition analysis of hydrophilic polymer layer | Moisture content change rate of substrate and device (%) | Contact angle (°) | Friction coefficient |
|---|---|---|---|---|---|---|---|---|---|
| Example 3 | A (30 seconds) | A (30 seconds) | A | 4.2 | Two layers | Coating polymer was separated into two layers (one layer of which was mixed with substrate) | 4.2 | 53.8 | 0.004 |
| Example 4 | B (19 seconds) | B (19 seconds) | A | 4.0 | Two layers | Coating polymer was separated into two layers (one layer of which was mixed with substrate) | 4.0 | 54.8 | 0.012 |
| Example 5 | B (19 seconds) | B (19 seconds) | A | 5.4 | Two layers | Coating polymer was separated into two layers (one layer of which was mixed with substrate) | 5.4 | 49.1 | 0.018 |
| Example 6 | A (40 seconds) | A (40 seconds) | A | 9.1 | Two layers | Coating polymer was separated into two layers (one layer of which was mixed with substrate) | 9.1 | 42.0 | 0.005 |
| Example 7 | A (120 seconds or more) | A (120 seconds or more) | A | 59 | Two layers | Coating polymer mixed with substrate and coating polymer alone | 1.0 | 40.7 | 0.009 |
| Example 8 | A (120 seconds or more) | A (120 seconds or more) | A | 58 | Two layers | Coating polymer mixed with substrate and coating polymer alone | 1.0 | 50.5 | 0.444 |
| Example 9 | A (120 seconds or more) | A (120 seconds or more) | A | 58 | Two layers | Coating polymer mixed with substrate and coating polymer alone | 0.8 | 51.8 | 0.611 |
| Example 10 | A (120 seconds or more) | A (120 seconds or more) | C | 58 | Two layers | Coating polymer mixed with substrate and coating polymer alone | 0.8 | 52.4 | 0.615 |
| Example 11 | A (120 seconds or more) | A (120 seconds or more) | A | 58 | Two layers | Coating polymer mixed with substrate and coating polymer alone | 1.1 | 39.0 | 0.300 |
| Example 12 | A (120 seconds or more) | A (120 seconds or more) | A | 58 | Two layers | Coating polymer mixed with substrate and coating polymer alone | 0.9 | 39.0 | 0.180 |
| Example 13 | A (120 seconds or more) | A (120 seconds or more) | A | 58 | Two layers | Coating polymer mixed with substrate and coating polymer alone | 0.8 | 38.3 | 0.050 |
| Example 14 | A (120 seconds or more) | A (120 seconds or more) | B | 58 | Two layers | Coating polymer mixed with substrate and coating polymer alone | 1.5 | 44.6 | 0.295 |
| Example 15 | A (120 seconds or more) | A (120 seconds or more) | B | 58 | Two layers | Coating polymer mixed with substrate and coating polymer alone | 1.1 | 54.6 | 0.090 |
| Example 16 | A (120 seconds or more) | A (120 seconds or more) | A | 58 | Two layers | Coating polymer mixed with substrate and coating polymer alone | 1.0 | 51.4 | 0.160 |
| Example 17 | A (100 seconds) | A (100 seconds) | A | 46.6 | Two layers | Coating polymer mixed with substrate and coating polymer alone | 0.6 | 46.3 | 0.220 |
| Example 18 | A (120 seconds or more) | A (120 seconds or more) | A | 46.4 | Two layers | Coating polymer mixed with substrate and coating polymer alone | 0.4 | 45.8 | 0.390 |
| Example 19 | A (87 seconds) | A (87 seconds) | A | 54.5 | Two layers | Coating polymer mixed with substrate and coating polymer alone | 0.5 | 48.0 | 0.03 |
| Example 20 | A (49 seconds) | A (49 seconds) | A | 54.6 | Two layers | Coating polymer mixed with substrate and coating polymer alone | 0.6 | 47.5 | 0.018 |
| Example 21 | A (79 seconds) | A (79 seconds) | A | 54.7 | Two layers | Coating polymer mixed with substrate and coating polymer alone | 0.7 | 47.8 | 0.024 |

TABLE 3

|  | Lipid deposition amount | Mucin deposition amount ($\mu g/cm^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Example 1 | Not deposited | 8.56 | 0.53 | 0.49 | −6.7 |
| Example 2 | Not deposited | 6.18 | 0.53 | 0.49 | −6.7 |
| Example 3 | Not deposited | 9.50 | 0.53 | 0.49 | −6.7 |
| Example 4 | Not deposited | 1.57 | 0.53 | 0.49 | −6.7 |
| Example 5 | Not deposited | 1.53 | 0.53 | 0.49 | −6.7 |
| Example 6 | Not deposited | 5.70 | 0.53 | 0.49 | −6.7 |
| Example 7 | Not deposited | 3.25 | 0.30 | 0.26 | −13.1 |
| Example 8 | Not deposited | 1.94 | 0.30 | 0.26 | −13.1 |
| Example 9 | Not deposited | 2.68 | 0.30 | 0.26 | −13.1 |
| Example 10 | Not deposited | 2.86 | 0.30 | 0.26 | −13.1 |
| Example 11 | Not deposited | 2.78 | 0.30 | 0.28 | −6.8 |
| Example 12 | Not deposited | 3.65 | 0.30 | 0.28 | −6.8 |
| Example 13 | Not deposited | 9.00 | 0.30 | 0.28 | −6.8 |
| Example 14 | Not deposited | 1.53 | 0.30 | 0.26 | −13.1 |
| Example 15 | Not deposited | 3.48 | 0.30 | 0.26 | −13.1 |
| Example 16 | Not deposited | 3.26 | 0.30 | 0.26 | −13.1 |
| Example 17 | Not deposited | 2.85 | 0.70 | 0.71 | 0.40 |
| Example 18 | Not deposited | 3.05 | 0.70 | 0.71 | 0.40 |
| Example 19 | Not deposited | 3.15 | 0.61 | 0.61 | 0.7 |
| Example 20 | Not deposited | 3.24 | 0.61 | 0.60 | −0.9 |
| Example 21 | Not deposited | 3.01 | 0.61 | 0.61 | 0.2 |

TABLE 4

|  | Size of substrate (mm) | Size of medical device (mm) | Size change rate due to formation of hydrophilic polymer layer (%) | Thickness of hydrophilic polymer layer of front curve surface - dry state - (nm) | Thickness of hydrophilic polymer layer of base curve surface - dry state - (nm) | Average thickness difference (%) | Thickness of hydrophilic polymer layer of front curve surface - frozen state - (nm) |
|---|---|---|---|---|---|---|---|
| Example 1 | 14.00 | 14.01 | 0.1 | 13.5 | 8.5 | 59 | 30 to 45 |
| Example 2 | 14.00 | 14.01 | 0.1 | 13.5 | 9.0 | 50 | 32 to 48 |
| Example 3 | 14.00 | 14.01 | 0.1 | 8.5 | 6.8 | 25 | 30 to 43 |
| Example 4 | 14.00 | 14.01 | 0.1 | 17.5 | 11.5 | 52 | 34 to 46 |
| Example 5 | 14.00 | 14.01 | 0.1 | 15.0 | 9.5 | 58 | 29 to 41 |
| Example 6 | 14.00 | 14.01 | 0.1 | 20.0 | 11.8 | 69 | 28 to 39 |
| Example 7 | 14.20 | 13.90 | −2.1 | 17.5 | 10.9 | 61 | 40 to 53 |
| Example 8 | 14.20 | 13.90 | −2.1 | 14.0 | 10.0 | 40 | 41 to 51 |
| Example 9 | 14.20 | 13.90 | −2.1 | 11.5 | 7.9 | 46 | 30 to 40 |
| Example 10 | 14.20 | 13.90 | −2.1 | 7.5 | 3.6 | 108 | 29 to 44 |
| Example 11 | 14.20 | 13.95 | −1.8 | 28.5 | 17.3 | 65 | 42 to 56 |
| Example 12 | 14.20 | 13.95 | −1.8 | 27.5 | 17.8 | 54 | 45 to 59 |
| Example 13 | 14.20 | 13.95 | −1.8 | 31.0 | 18.1 | 71 | 40 to 50 |
| Example 14 | 14.20 | 13.90 | −2.1 | 29.5 | 16.9 | 75 | 40 to 55 |
| Example 15 | 14.20 | 13.90 | −2.1 | 30.0 | 18.0 | 67 | 35 to 45 |
| Example 16 | 14.20 | 13.90 | −2.1 | 27.5 | 16.1 | 71 | 40 to 51 |
| Example 17 | 14.20 | 14.23 | 0.2 | 13.5 | 8.5 | 59 | 70 to 98 |
| Example 18 | 14.20 | 14.23 | 0.2 | 15.0 | 9.9 | 52 | 80 to 95 |
| Example 19 | 14.20 | 14.12 | −0.6 | 12.5 | 8.9 | 40 | 40 to 50 |
| Example 20 | 14.20 | 14.14 | −0.4 | 12.5 | 8.1 | 54 | 42 to 50 |
| Example 21 | 14.20 | 14.13 | −0.5 | 12.0 | 6.9 | 74 | 30 to 42 |

Example 22

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. An aqueous solution containing 0.2% by mass of an acrylic acid/vinylpyrrolidone/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 2.6 with sulfuric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 23

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/2-hydroxyethyl methacrylate/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 2.6 with sulfuric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 24

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/2-hydroxyethyl methacrylate/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 3.1 with citric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 25

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.1 with citric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 26

A commercially available silicone hydrogel lens containing silicone as a main component "Biofinity (registered trademark)" (comfilcon A, manufactured by CooperVision Inc.) was used as a substrate. An aqueous solution containing 0.2% by mass of an acrylic acid/2-hydroxyethyl methacrylate/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 2.9 with sulfuric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 27

A commercially available silicone hydrogel lens containing silicone as a main component "Biofinity (registered trademark)" (comfilcon A, manufactured by CooperVision Inc.) was used as a substrate. An aqueous solution containing 0.2% by mass of an acrylic acid/2-hydroxyethyl methacrylate/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 3.3 with citric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 28

A commercially available silicone hydrogel lens containing silicone as a main component "Biofinity (registered trademark)" (comfilcon A, manufactured by CooperVision Inc.) was used as a substrate. An aqueous solution containing 0.2% by mass of an acrylic acid/vinylpyrrolidone/N,N-dimethylacrylamide copolymer (number ratio of basic group/acidic group: 0, molar ratio in copolymerization: 1/1/8, Mw: 500,000, manufactured by Osaka Organic Chemical Industry Ltd.) in a phosphate buffer solution was adjusted to pH 3.1 with citric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 29

A commercially available silicone hydrogel lens containing silicone as a main component "Biofinity (registered trademark)" (comfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with citric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 30

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with formic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 31

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with acetic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 32

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with propionic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 33

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with butyric acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 34

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with glycolic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 35

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with lactic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 36

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with malic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

Example 37

A commercially available silicone hydrogel lens containing silicone as a main component "MyDay (registered trademark)" (stenfilcon A, manufactured by CooperVision Inc.) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution was adjusted to pH 3.2 with ascorbic acid. The substrate was immersed in the solution, followed by heating in an autoclave at 121° C. for 30 minutes. The molded body thus obtained was washed with a phosphate buffer solution while immersing for 30 seconds and, after replacing by a fresh phosphate buffer solution, the molded body was further heated in the autoclave at 121° C. for 30 minutes. The results obtained by evaluation of the molded body thus obtained using the above method are shown in Tables 5 to 8.

TABLE 5

| | Substrate | Moisture content of substrate (%) | Hydrophilic polymer and concentration of solution thereof | Initial pH | pH after heating treatment |
|---|---|---|---|---|---|
| Example 22 | "1-Day Acuvue TruEye ®" | 48 | 0.2% by mass Acrylic acid/vinylpyrrolidone/N,N-dimethylacrylamide copolymer | 2.6 | 5.0 |
| Example 23 | "MyDay ®" | 54 | 0.2% by mass Acrylic acid/2-hydroxyethyl methacrylate/N,N-dimethylacrylamide copolymer | 2.1 | 3.4 |
| Example 24 | "MyDay ®" | 54 | 0.2% by mass Acrylic acid/2-hydroxyethyl methacrylate/N,N-dimethylacrylamide copolymer | 3.1 | 3.4 |
| Example 25 | "MyDay ®" | 54 | 0.2% by mass Acrylic acid/N,N-dimethylacrylamide copolymer | 3.1 | 3.6 |
| Example 26 | "Biofinity ®" | 48 | 0.2% by mass Acrylic acid/2-hydroxyethyl methacrylate/N,N-dimethylacrylamide copolymer | 2.9 | 4.2 |
| Example 27 | "Biofinity ®" | 48 | 0.2% by mass Acrylic acid/2-hydroxyethyl methacrylate/N,N-dimethylacrylamide copolymer | 3.3 | 3.7 |
| Example 28 | "Biofinity ®" | 48 | 0.2% by mass Acrylic acid/vinylpyrrolidone/N,N-dimethylacrylamide copolymer | 3.1 | 3.4 |
| Example 29 | "Biofinity ®" | 48 | 0.2% by mass Acrylic acid/N,N-dimethylacrylamide copolymer | 3.2 | 3.8 |
| Example 30 | "MyDay ®" | 54 | 0.2% by mass Acrylic acid/N,N-dimethylacrylamide copolymer | 3.2 | 3.4 |
| Example 31 | "MyDay ®" | 54 | 0.2% by mass Acrylic acid/N,N-dimethylacrylamide copolymer | 3.2 | 3.6 |
| Example 32 | "MyDay ®" | 54 | 0.2% by mass Acrylic acid/N,N-dimethylacrylamide copolymer | 3.2 | 3.4 |
| Example 33 | "MyDay ®" | 54 | 0.2% by mass Acrylic acid/N,N-dimethylacrylamide copolymer | 3.2 | 3.4 |
| Example 34 | "MyDay ®" | 54 | 0.2% by mass Acrylic acid/N,N-dimethylacrylamide copolymer | 3.2 | 3.4 |
| Example 35 | "MyDay ®" | 54 | 0.2% by mass Acrylic acid/N,N-dimethylacrylamide copolymer | 3.2 | 3.5 |
| Example 36 | "MyDay ®" | 54 | 0.2% by mass Acrylic acid/N,N-dimethylacrylamide copolymer | 3.2 | 3.6 |
| Example 37 | "MyDay ®" | 54 | 0.2% by mass Acrylic acid/N,N-dimethylacrylamide copolymer | 3.2 | 3.3 |

TABLE 6

| | Liquid film retention time (seconds) | Liquid film retention time at 40 minutes after ultrasonic cleaning (seconds) | Lubricity | Moisture content of medical device (%) | Number of hydrophilic polymer layers | Results of elemental composition analysis of hydrophilic polymer layer | Moisture content change rate of substrate and device | Contact angle (°) | Friction coefficient |
|---|---|---|---|---|---|---|---|---|---|
| Example 22 | A (120 seconds) | A (120 seconds) | A | 47.8 | Two layers | Coating polymer was separated into two layers (one layer of which was mixed with substrate) | 1.8 | 45.6 | 0.002 |

TABLE 6-continued

|  | Liquid film retention time (seconds) | Liquid film retention time at 40 minutes after ultrasonic cleaning (seconds) | Lubricity | Moisture content of medical device (%) | Number of hydrophilic polymer layers | Results of elemental composition analysis of hydrophilic polymer layer | Moisture content change rate of substrate and device | Contact angle (°) | Friction coefficient |
|---|---|---|---|---|---|---|---|---|---|
| Example 23 | A (40 seconds) | A (40 seconds) | A | 55.0 | Two layers | Coating polymer was separated into two layers (one layer of which was mixed with substrate) | 1.0 | 47.0 | 0.015 |
| Example 24 | A (40 seconds) | A (40 seconds) | A | 55.2 | Two layers | Coating polymer was separated into two layers (one layer of which was mixed with substrate) | 1.2 | 46.5 | 0.018 |
| Example 25 | A (120 seconds) | A (120 seconds) | A | 55.9 | Two layers | Coating polymer was separated into two layers (one layer of which was mixed with substrate) | 1.9 | 46.3 | 0.010 |
| Example 26 | A (80 seconds) | A (80 seconds) | A | 49.0 | Two layers | Coating polymer was separated into two layers (one layer of which was mixed with substrate) | 1.0 | 46.1 | 0.010 |
| Example 27 | A (120 seconds) | A (120 seconds) | A | 49.2 | Two layers | Coating polymer was separated into two layers (one layer of which was mixed with substrate) | 1.2 | 46.0 | 0.016 |
| Example 28 | A (120 seconds) | A (120 seconds) | A | 49.5 | Two layers | Coating polymer mixed with substrate and coating polymer alone | 1.5 | 45.9 | 0.011 |
| Example 29 | A (120 seconds) | A (120 seconds) | A | 49.7 | Two layers | Coating polymer mixed with substrate and coating polymer alone | 1.7 | 46.7 | 0.009 |
| Example 30 | A (120 seconds) | A (120 seconds) | A | 55.6 | Two layers | Coating polymer mixed with substrate and coating polymer alone | 1.6 | 45.9 | 0.018 |
| Example 31 | A (25 seconds) | A (25 seconds) | C | 55.4 | Two layers | Coating polymer mixed with substrate and coating polymer alone | 1.4 | 44.9 | 0.015 |
| Example 32 | A (31 seconds or more) | A (31 seconds or more) | A | 54.7 | Two layers | Coating polymer mixed with substrate and coating polymer alone | 0.7 | 48.7 | 0.019 |
| Example 33 | A (27 seconds) | A (27 seconds) | A | 54.9 | Two layers | Coating polymer mixed with substrate and coating polymer alone | 0.9 | 49.9 | 0.016 |
| Example 34 | A (42 seconds) | A (42 seconds) | A | 54.5 | Two layers | Coating polymer mixed with substrate and coating polymer alone | 0.5 | 46.0 | 0.016 |
| Example 35 | A (23 seconds) | A (23 seconds) | B | 54.4 | Two layers | Coating polymer mixed with substrate and coating polymer alone | 0.4 | 50.0 | 0.043 |
| Example 36 | A (82 seconds) | A (82 seconds) | B | 55.0 | Two layers | Coating polymer mixed with substrate and coating polymer alone | 1.0 | 45.8 | 0.014 |
| Example 37 | A (120 seconds) | A (120 seconds) | A | 55.2 | Two layers | Coating polymer mixed with substrate and coating polymer alone | 1.2 | 45.0 | 0.045 |

TABLE 7

|  | Lipid deposition amount | Mucin deposition amount (μg/cm$^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Example 22 | Not deposited | 3.00 | 0.70 | 0.71 | 0.40 |
| Example 23 | Not deposited | 3.03 | 0.61 | 0.62 | 1.4 |
| Example 24 | Not deposited | 2.99 | 0.61 | 0.61 | 0.2 |
| Example 25 | Not deposited | 3.02 | 0.61 | 0.61 | 0.2 |
| Example 26 | Not deposited | 3.02 | 0.62 | 0.61 | −1.1 |

TABLE 7-continued

| | Lipid deposition amount | Mucin deposition amount ($\mu g/cm^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Example 27 | Not deposited | 3.10 | 0.62 | 0.63 | 1.8 |
| Example 28 | Not deposited | 3.25 | 0.62 | 0.61 | −1.0 |
| Example 29 | Not deposited | 3.17 | 0.62 | 0.63 | 1.8 |
| Example 30 | Not deposited | 3.50 | 0.61 | 0.62 | 1.4 |
| Example 31 | Not deposited | 3.09 | 0.61 | 0.61 | 0.2 |
| Example 32 | Not deposited | 2.89 | 0.61 | 0.61 | 0.2 |
| Example 33 | Not deposited | 3.60 | 0.61 | 0.61 | 0.2 |
| Example 34 | Not deposited | 3.00 | 0.61 | 0.61 | 0.2 |
| Example 35 | Not deposited | 3.62 | 0.61 | 0.61 | 0.2 |
| Example 36 | Not deposited | 2.99 | 0.61 | 0.61 | 0.2 |
| Example 37 | Not deposited | 2.85 | 0.61 | 0.61 | 0.2 |

TABLE 8

| | Size of substrate (mm) | Size of medical device (mm) | Size change rate due to formation of hydrophilic polymer layer (%) | Thickness of hydrophilic polymer layer of front curve surface - dry state - (nm) | Thickness of hydrophilic polymer layer of base curve surface - dry state - (nm) | Average thickness difference (%) | Thickness of hydrophilic polymer layer of front curve surface - frozen state - (nm) |
|---|---|---|---|---|---|---|---|
| Example 22 | 14.20 | 14.25 | 0.4 | 13.8 | 9.0 | 53 | 69 to 98 |
| Example 23 | 14.20 | 14.18 | −0.1 | 11.8 | 8.0 | 48 | 40 to 65 |
| Example 24 | 14.20 | 14.10 | −0.7 | 14.0 | 9.6 | 46 | 38 to 66 |
| Example 25 | 14.20 | 14.15 | −0.4 | 15.0 | 10.3 | 46 | 40 to 70 |
| Example 26 | 14.00 | 13.90 | −0.7 | 16.5 | 10.9 | 51 | 45 to 71 |
| Example 27 | 14.00 | 13.85 | −1.1 | 17.2 | 11.3 | 52 | 48 to 74 |
| Example 28 | 14.00 | 13.90 | −0.7 | 16.9 | 11.8 | 43 | 46 to 72 |
| Example 29 | 14.00 | 13.91 | −0.6 | 17.3 | 11.6 | 49 | 50 to 75 |
| Example 30 | 14.20 | 14.10 | −0.7 | 12.0 | 8.8 | 36 | 43 to 58 |
| Example 31 | 14.20 | 14.06 | −1.0 | 10.0 | 7.9 | 27 | 30 to 49 |
| Example 32 | 14.20 | 14.13 | −0.5 | 10.1 | 7.2 | 40 | 32 to 44 |
| Example 33 | 14.20 | 14.01 | −1.3 | 10.3 | 8.0 | 29 | 31 to 46 |
| Example 34 | 14.20 | 14.07 | −0.9 | 11.5 | 9.0 | 28 | 33 to 47 |
| Example 35 | 14.20 | 14.02 | −1.3 | 10.3 | 8.0 | 29 | 32 to 45 |
| Example 36 | 14.20 | 14.00 | −1.4 | 13.2 | 9.9 | 33 | 45 to 61 |
| Example 37 | 14.20 | 14.04 | −1.1 | 13.4 | 9.9 | 35 | 46 to 71 |

Comparative Example 1

The molded body obtained in Reference Example 1 was used as a substrate. The substrate was immersed in a solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 2

The molded body obtained in Reference Example 1 was used as a substrate. The substrate was immersed in a solution in which the pH of a phosphate buffer solution was adjusted to 2.7 with sulfuric acid, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained using the above method are shown in Tables 9 to 12.

Comparative Example 3

The molded body obtained in Reference Example 1 was used as a substrate. The substrate was immersed in a solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution (pH 6.8) at room temperature (23° C.) and then left to stand overnight. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 4

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in a phosphate buffer solution (pH 6.8) at room temperature (23° C.) and then left to stand overnight. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 5

The molded body obtained in Reference Example 1 was used as a substrate. The substrate was immersed in a solution containing 0.1% by mass of polyacrylic acid "Sokalan (registered trademark) PA110S" (number ratio of basic group/acidic group: 0, Mw: 250,000, manufactured by BASF Corporation) in a phosphate buffer (pH 5.3), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 6

The molded body obtained in Reference Example 1 was used as a substrate. A solution containing 0.2% by mass of polydimethylacrylamide (number ratio of basic group/acidic group: 0, Mw: 360,000, manufactured by Osaka Organic Chemical Industry Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 7

The molded body obtained in Reference Example 1 was used as a substrate. A solution containing 0.2% by mass of polyvinylpyrrolidone K-90 (number ratio of basic group/acidic group: 0, Mw: 360,000, manufactured by Tokyo Chemical Industry Co., Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 8

The molded body obtained in Reference Example 1 was used as a substrate. A solution containing 0.2% by mass of Polyethylene Glycol 200 (number ratio of basic group/acidic group: 0, Mw: 180 to 200, manufactured by Wako Pure Chemical Industries, Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 9

The molded body obtained in Reference Example 1 was used as a substrate. A solution containing 0.2% by mass of poly-N-vinylacetamide "GE-191-103" (number ratio of basic group/acidic group: 0, Mw: 1,000,000, manufactured by Showa Denko K.K.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 10

The molded body obtained in Reference Example 1 was used as a substrate. After making a trial of immersing the substrate in a solution containing 0.1% by mass of polyvinyl alcohol (number ratio of basic group/acidic group: 0, Mw: 31,000 to 50,000, manufactured by SIGMA-ALDRICH) in a phosphate buffer solution, a precipitate was formed in the solution due to inferior solubility of polyvinyl alcohol, thus failing to perform coating.

Comparative Example 11

The molded body obtained in Reference Example 1 was used as a substrate. A solution containing 0.2% by mass of "Methyl Cellulose 400" (number ratio of basic group/acidic group: 0, Mw: 84,000, manufactured by Wako Pure Chemical Industries, Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 12

The molded body obtained in Reference Example 1 was used as a substrate. A solution containing 0.2% by mass of Poloxamer 407 (number ratio of basic group/acidic group: 0, Mw: 11,500, manufactured by BASF Corporation) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 13

The molded body obtained in Reference Example 1 was used as a substrate. A solution containing 0.2% by mass of sodium alginate (number ratio of basic group/acidic group: 0, manufactured by SHOWA CHEMICAL CO., LTD.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 14

The molded body obtained in Reference Example 1 was used as a substrate. The substrate was immersed in a solution containing 0.05% by mass of poly-2-acrylamido-2-methyl-propanesulfonic acid (number ratio of basic group/acidic group: 0, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 15

The molded body obtained in Reference Example 1 was used as a substrate. The substrate was immersed in a solution containing 0.05% by mass of poly-2-acrylamido-2-methyl-propanesulfonic acid/N,N-dimethylacrylamide copolymer (number ratio of basic group/acidic group: 0, molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 16

The molded body obtained in Reference Example 1 was used as a substrate. A solution containing 0.2% by mass of a polyvinyl acetate/polyvinylpyrrolidone copolymer "PVA-6450" (number ratio of basic group/acidic group: 0, Mw: 50,000, manufactured by Osaka Organic Chemical Industry Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 17

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of a polyvinyl acetate/polyvinylpyrrolidone copolymer "PVA-6450" (number ratio of basic group/acidic group: 0, Mw: 50,000, manufactured by Osaka Organic Chemical Industry Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 18

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of a polyvinyl acetate/polyvinylpyrrolidone copolymer "PVA-6450" (number ratio of basic group/acidic group: 0, Mw: 50,000, manufactured by Osaka Organic Chemical Industry Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 19

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of poly-N-vinylacetamide "GE-191-103" (number ratio of basic group/acidic group: 0, Mw: 1,000,000, manufactured by Showa Denko K.K.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 20

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of poly-N-vinylacetamide "GE-191-103" (number ratio of basic group/acidic group: 0, Mw: 1,000,000, manufactured by Showa Denko K.K.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

Comparative Example 21

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of sodium alginate (number ratio of basic group/acidic group: 0, manufactured by SHOWA CHEMICAL CO., LTD.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 9 to 12.

TABLE 9

| | Substrate | Moisture content of substrate (%) | Hydrophilic polymer and concentration of solution thereof | Initial pH | pH after heating treatment |
|---|---|---|---|---|---|
| Comparative Example 1 | Reference Example 1 | Less than 1% | 0.2% by mass Acrylic acid/N,N-dimethylacrylamide copolymer | 6.8 | 6.9 |
| Comparative Example 2 | Reference Example 1 | Less than 1% | Containing no polymer | 2.7 | 2.8 |
| Comparative Example 3 | Reference Example 1 | Less than 1% | 0.2% by mass Acrylic acid/N,N-dimethylacrylamide copolymer | 6.8 | 6.8 |
| Comparative Example 4 | "1-Day Acuvue ®" | 58 | 0.2% by mass Acrylic acid/N,N-dimethylacrylamide copolymer | 6.8 | 6.9 |
| Comparative Example 5 | Reference Example 1 | Less than 1% | 0.1% by mass Polyacrylic acid | 5.3 | 5.3 |
| Comparative Example 6 | Reference Example 1 | Less than 1% | 0.2% by mass Polydimethylacrylamide | 2.5 | 2.5 |
| Comparative Example 7 | Reference Example 1 | Less than 1% | 0.2% by mass Polyvinylpyrrolidone | 2.5 | 2.5 |
| Comparative Example 8 | Reference Example 1 | Less than 1% | 0.2% by mass Polyethylene glycol 200 | 2.5 | 2.5 |
| Comparative Example 9 | Reference Example 1 | Less than 1% | 0.2% by mass Poly-N-vinylacetamide | 2.5 | 2.5 |
| Comparative Example 10 | Reference Example 1 | Less than 1% | 0.1% by mass Polyvinyl alcohol | *Impossible to perform coating due to inferior solubility | *Impossible to perform coating due to inferior solubility |
| Comparative Example 11 | Reference Example 1 | Less than 1% | 0.2% by mass Methyl Cellulose 400 | 2.5 | 2.5 |
| Comparative Example 12 | Reference Example 1 | Less than 1% | 0.2% by mass Poloxamer 407 | 2.5 | 2.5 |
| Comparative Example 13 | Reference Example 1 | Less than 1% | 0.2% by mass Sodium alginate | 2.5 | 2.5 |
| Comparative Example 14 | Reference Example 1 | Less than 1% | 0.05% by mass Poly-2-acrylamido-2-methylpropanesulfonic acid | 6.8 | 6.9 |

TABLE 9-continued

|  | Substrate | Moisture content of substrate (%) | Hydrophilic polymer and concentration of solution thereof | Initial pH | pH after heating treatment |
|---|---|---|---|---|---|
| Comparative Example 15 | Reference Example 1 | Less than 1% | 0.05% by mass 2-Acrylamido-2-methylpropanesulfonic acid/N,Ndimethylacrylamide copolymer | 6.8 | 6.9 |
| Comparative Example 16 | Reference Example 1 | Less than 1% | 0.2% by mass Vinylpyrrolidone/vinyl acetate copolymer | 2.5 | 2.4 |
| Comparative Example 17 | "1-Day Acuvue ®" | 58 | 0.2% by mass Vinylpyrrolidone/vinyl acetate copolymer | 2.5 | 2.6 |
| Comparative Example 18 | "1-Day Acuvue TruEye ®" | 46 | 0.2% by mass Vinylpyrrolidone/vinyl acetate copolymer | 2.5 | 2.6 |
| Comparative Example 19 | "1-Day Acuvue ®" | 58 | 0.2% by mass Poly-N-vinylacetamide | 2.5 | 2.5 |
| Comparative Example 20 | "1-Day Acuvue TruEye ®" | 46 | 0.2% by mass Poly-N-vinylacetamide | 2.5 | 2.5 |
| Comparative Example 21 | "1-Day Acuvue ®" | 58 | 0.2% by mass Sodium alginate | 2.5 | 2.6 |

TABLE 10

|  | Liquid film retention time (seconds) | Liquid film retention time at 40 minutes after ultrasonic cleaning (seconds) | Lubricity | Moisture content of medical device (%) | Number of hydrophilic polymer layers | Moisture content change rate of substrate and device (%) | Contact angle (°) | Friction coefficient |
|---|---|---|---|---|---|---|---|---|
| Comparative Example 1 | E (0 second) | E (0 second) | D | Less than 1% | Impossible to confirm layer | 0 | 83.0 | 0.850 |
| Comparative Example 2 | E (0 second) | E (0 second) | E | Less than 1% | 0 Layer | None | 81.9 | 0.852 |
| Comparative Example 3 | E (0 second) | E (0 second) | E | Less than 1% | Impossible to confirm layer | 0 | 80.0 | 0.852 |
| Comparative Example 4 | A (20 seconds) | A (20 seconds) | E | 58% | Impossible to confirm layer | 0 | 54.0 | 0.677 |
| Comparative Example 5 | E (0 second) | E (0 second) | E | Less than 1% | Impossible to confirm layer | 0 | 79.0 | 0.849 |
| Comparative Example 6 | E (0 second) | E (0 second) | E | Less than 1% | Impossible to confirm layer | 0 | 82.0 | 0.840 |
| Comparative Example 7 | E (0 second) | E (0 second) | E | Less than 1% | Impossible to confirm layer | 0 | 80.9 | 0.839 |
| Comparative Example 8 | E (0 second) | E (0 second) | E | Less than 1% | Impossible to confirm layer | 0 | 81.9 | 0.850 |
| Comparative Example 9 | E (0 second) | E (0 second) | E | Less than 1% | Impossible to confirm layer | 0 | 83.5 | 0.830 |
| Comparative Example 10 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 11 | E (0 second) | E (0 second) | E | Less than 1% | Impossible to confirm layer | 0 | 83.0 | 0.860 |
| Comparative Example 12 | E (0 second) | E (0 second) | E | Less than 1% | Impossible to confirm layer | 0 | 82.9 | 0.841 |
| Comparative Example 13 | E (0 second) | E (0 second) | E | Less than 1% | Impossible to confirm layer | 0 | 80.1 | 0.852 |
| Comparative Example 14 | E (0 second) | E (0 second) | E | Less than 1% | Impossible to confirm layer | 0 | 78.0 | 0.854 |
| Comparative Example 15 | E (0 second) | E (0 second) | E | Less than 1% | Impossible to confirm layer | 0 | 81.7 | 0.830 |
| Comparative Example 16 | E (0 second) | E (0 second) | E | Less than 1% | Impossible to confirm layer | 0 | 80.0 | 0.820 |
| Comparative Example 17 | A (20 seconds) | A (20 seconds) | D | 58 | Impossible to confirm layer | 0 | 53.5 | 0.450 |
| Comparative Example 18 | C (12 seconds) | D (12 seconds) | C | 46 | Impossible to confirm layer | 0 | 48.0 | 0.130 |
| Comparative Example 19 | C (10 seconds) | C (5 seconds) | D | 58 | Impossible to confirm layer | 0 | 54.0 | 0.470 |

TABLE 10-continued

|  | Liquid film retention time (seconds) | Liquid film retention time at 40 minutes after ultrasonic cleaning (seconds) | Lubricity | Moisture content of medical device (%) | Number of hydrophilic polymer layers | Moisture content change rate of substrate and device (%) | Contact angle (°) | Friction coefficient |
|---|---|---|---|---|---|---|---|---|
| Comparative Example 20 | C (12 seconds) | C (5 seconds) | C | 46 | Impossible to confirm layer | 0 | 47.0 | 0.120 |
| Comparative Example 21 | C (10 seconds) | C (3 seconds) | D | 58 | Impossible to confirm layer | 0 | 53.9 | 0.419 |

TABLE 11

|  | Lipid deposition amount | Mucin deposition amount (μg/cm$^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Comparative Example 1 | Deposited on entire area | 3.20 | 0.53 | 0.49 | −6.8 |
| Comparative Example 2 | Deposited on entire area | 3.00 | 0.53 | None | None |
| Comparative Example 3 | Deposited on entire area | 2.95 | 0.53 | 0.49 | −6.8 |
| Comparative Example 4 | Not deposited | 2.88 | 0.30 | 0.28 | −6.8 |
| Comparative Example 5 | Deposited on entire area | 3.35 | 0.53 | 0.49 | −6.8 |
| Comparative Example 6 | Deposited on entire area | 3.00 | 0.53 | 0.49 | −6.8 |
| Comparative Example 7 | Deposited on entire area | 3.10 | 0.53 | 0.49 | −6.8 |
| Comparative Example 8 | Deposited on entire area | 2.98 | 0.53 | 0.49 | −6.8 |
| Comparative Example 9 | Deposited on entire area | 3.40 | 0.53 | 0.49 | −6.8 |
| Comparative Example 10 | *Impossible to perform coating due to inferior solubility | *Impossible to perform coating due to inferior solubility | 0.53 | *Impossible to perform coating due to inferior solubility | *Impossible to perform coating due to inferior solubility |
| Comparative Example 11 | Deposited on entire area | 3.29 | 0.53 | 0.49 | −6.8 |
| Comparative Example 12 | Deposited on entire area | 2.99 | 0.53 | 0.49 | −6.8 |
| Comparative Example 13 | Deposited on entire area | 3.04 | 0.53 | 0.49 | −6.8 |
| Comparative Example 14 | Deposited on entire area | 3.00 | 0.53 | 0.49 | −6.8 |
| Comparative Example 15 | Deposited on entire area | 3.30 | 0.53 | 0.49 | −6.8 |
| Comparative Example 16 | Deposited on entire area | 2.91 | 0.42 | 0.49 | 15.1 |
| Comparative Example 17 | Not deposited | 2.25 | 0.30 | 0.28 | −7.7 |
| Comparative Example 18 | Deposited in area accounting for 1/5 of entire area | 1.00 | 0.70 | 0.60 | −15.3 |
| Comparative Example 19 | Not deposited | 2.30 | 0.30 | 0.29 | −4.4 |
| Comparative Example 20 | Deposited in area accounting for 1/5 of entire area | 1.10 | 0.70 | 0.71 | 0.40 |
| Comparative Example 21 | Not deposited | 2.20 | 0.30 | 0.29 | −4.4 |

TABLE 12

| | Size of substrate (mm) | Size of medical device (mm) | Size change rate due to formation of hydrophilic polymer layer (%) | Thickness of hydrophilic polymer layer of front curve surface - dry state - (nm) | Thickness of hydrophilic polymer layer of base curve surface - dry state - (nm) | Average thickness difference (%) | Thickness of hydrophilic polymer layer of front curve surface - frozen state - (nm) |
|---|---|---|---|---|---|---|---|
| Comparative Example 1 | 14.00 | 14.01 | 0.1 | 0 | 0 | 0 | 0 |
| Comparative Example 2 | 14.00 | None | None | 0 | 0 | 0 | 0 |
| Comparative Example 3 | 14.00 | 14.01 | 0.1 | 0 | 0 | 0 | 0 |
| Comparative Example 4 | 14.20 | 14.05 | −1.1 | 0 | 0 | 0 | 0 |
| Comparative Example 5 | 14.00 | 14.00 | 0.0 | 0 | 0 | 0 | 0 |
| Comparative Example 6 | 14.00 | 14.00 | 0.0 | 0 | 0 | 0 | 0 |
| Comparative Example 7 | 14.00 | 14.00 | 0.0 | 0 | 0 | 0 | 0 |
| Comparative Example 8 | 14.00 | 14.00 | 0.0 | 0 | 0 | 0 | 0 |
| Comparative Example 9 | 14.00 | 14.00 | 0.0 | 0 | 0 | 0 | 0 |
| Comparative Example 10 | 14.00 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 11 | 14.00 | 14.00 | 0.0 | 0 | 0 | 0 | 0 |
| Comparative Example 12 | 14.00 | 14.00 | 0.0 | 0 | 0 | 0 | 0 |
| Comparative Example 13 | 14.00 | 14.00 | 0.0 | 0 | 0 | 0 | 0 |
| Comparative Example 14 | 14.00 | 14.00 | 0.0 | 0 | 0 | 0 | 0 |
| Comparative Example 15 | 14.00 | 14.00 | 0.0 | 0 | 0 | 0 | 0 |
| Comparative Example 16 | 14.00 | 14.00 | 0.0 | 0 | 0 | 0 | 0 |
| Comparative Example 17 | 14.20 | 13.90 | −2.1 | 0 | 0 | 0 | 0 |
| Comparative Example 18 | 14.20 | 14.3 | 0.7 | 0 | 0 | 0 | 0 |
| Comparative Example 19 | 14.20 | 14.10 | −0.7 | 0 | 0 | 0 | 0 |
| Comparative Example 20 | 14.20 | 14.20 | 0.0 | 0 | 0 | 0 | 0 |
| Comparative Example 21 | 14.20 | 14.10 | −0.7 | 0 | 0 | 0 | 0 |

Comparative Example 22

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of sodium alginate (number ratio of basic group/acidic group: 0, manufactured by SHOWA CHEMICAL CO., LTD.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 23

A commercially available hydrogel lens containing 2-hydroxyethyl methacrylate as a main component "1-Day Acuvue (registered trademark)" (etafilcon A, manufactured by Johnson & Johnson) was used as a substrate. A solution containing 0.2% by mass of Poloxamer 407 (number ratio of basic group/acidic group: 0, Mw: 11,500, manufactured by BASF Corporation) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 24

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. A solution containing 0.2% by mass of Poloxamer 407 (number ratio of basic group/acidic group: 0, Mw: 11,500, manufactured by BASF Japan Ltd.) in a phosphate buffer solution was adjusted to pH 2.5 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 25

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution containing 0.05% by mass of poly-2-acrylamido-2-methylpropanesulfonic acid (number ratio of basic group/acidic group: 0, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 26

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in a solution containing 0.05% by mass of poly-2-acrylamido-2-methylpropanesulfonic acid (number ratio of basic group/acidic group: 0, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 27

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution containing 0.05% by mass of a poly-2-acrylamido-2-methylpropanesulfonic acid/N,N-dimethylacrylamide copolymer (number ratio of basic group/acidic group: 0, molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 28

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in a solution containing 0.05% by mass of a poly-2-acrylamido-2-methylpropanesulfonic acid/N,N-dimethylacrylamide copolymer (number ratio of basic group/acidic group: 0, molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 29

The molded body obtained in Reference Example 1 was used as a substrate. An aqueous solution containing 0.1% by mass of an acrylic acid/vinylpyrrolidone copolymer (number ratio of basic group/acidic group: 0, molar ratio in copolymerization: 1/9, Mw: 400,000, manufactured by Osaka Organic Chemical Industry Ltd.) and 0.3% by mass of urea in pure water was adjusted to pH 3.8 with sulfuric acid. The substrate was immersed in the solution, followed by heating in an autoclave at 121° C. for 30 minutes. The molded body thus obtained was washed with a phosphate buffer solution while shaking at 250 rpm for 30 seconds and, after replacing by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 30

A commercially available hydrogel lens containing 2-hydroxyethyl methacrylate as a main component "Medalist (registered trademark) 1DAY PLUS" (hilafilcon B, manufactured by Bausch & Lomb Incorporated) was used as a substrate. An aqueous solution containing 0.1% by mass of an acrylic acid/vinylpyrrolidone copolymer (number ratio of basic group/acidic group: 0, molar ratio in copolymerization: 1/9, Mw: 400,000, manufactured by Osaka Organic Chemical Industry Ltd.) and 0.3% by mass of urea in pure water was adjusted to pH 3.8 with sulfuric acid. The substrate was immersed in the solution, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 31

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) and 0.3% by mass of urea in pure water was adjusted to pH 3.0 with sulfuric acid. The substrate was immersed in the solution, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 13 to 16.

Comparative Example 32

The results obtained by evaluation of a commercially available hydrogel lens containing 2-hydroxyethyl methacrylate as a main component "1-Day Acuvue (registered trademark)" (etafilcon A, manufactured by Johnson & Johnson) using the above method are shown in Tables 13 to 16.

Comparative Example 33

The results obtained by evaluation of a commercially available silicone hydrogel lens containing polyvinylpyrrolidone and silicone as main components "1-Day Acuvue TruEye (registered trademark)" (narafilcon A, manufactured by Johnson & Johnson) using the above method are shown in Tables 13 to 16.

Comparative Example 34

The results obtained by evaluation of a commercially available silicone hydrogel lens containing polyvinylpyrrolidone and silicone as main components "Acuvue Oasys (registered trademark)" (senofilcon A, manufactured by Johnson & Johnson) using the above method are shown in Tables 13 to 16.

Comparative Example 35

The results obtained by evaluation of a commercially available silicone hydrogel lens, which has a surface subjected to a plasma treatment and contains silicone as a main component "AIR OPTIX EXAQUA (registered trademark)" (lotrafilcon B, manufactured by Alcon Japan Ltd.), using the above method are shown in Tables 13 to 16.

Comparative Example 36

The results obtained by evaluation of a commercially available hydrogel lens containing 2-hydroxyethyl methacrylate obtained by copolymerizing an MPC monomer (2-methacryloyloxyethylphosphorylcholine) as a main component "Proclear 1 Day" (omafilcon A, manufactured by Cooper Vision) using the above method are shown in Tables 13 to 16.

Comparative Example 37

The molded body obtained in Reference Example 1 was used as a substrate. The substrate was immersed in a solution containing 1.2% by mass of polyacrylic acid "Sokalan (registered trademark) PA110S" (number ratio of basic group/acidic group: 0, Mw: 250,000, manufactured by BASF Corporation) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 38

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution containing 1.2% by mass of polyacrylic acid "Sokalan (registered trademark) PA110S" (number ratio of basic group/acidic group: 0, Mw: 250,000, manufactured by BASF Japan Ltd.) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 39

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in a solution containing 1.2% by mass of polyacrylic acid "Sokalan (registered trademark) PA110S" (number ratio of basic group/ acidic group: 0, Mw: 250,000, manufactured by BASF Corporation) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 40

The molded body obtained in Reference Example 1 was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (number ratio of basic group/acidic group: 0, Mw: 250,000, manufactured by BASF Corporation) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 41

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (number ratio of basic group/acidic group: 0, Mw: 250,000, manufactured by BASF Corporation) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 42

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (number ratio of basic group/acidic group: 0, Mw: 250,000, manufactured by BASF Corporation) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body thus obtained (a hydrophilic polymer layer was not confirmed) using the above method are shown in Tables 13 to 16.

Comparative Example 43

The molded body obtained in Reference Example 1 was used as a substrate. After making a trial of immersing the substrate in a solution containing 0.1% by mass of chitosan (0.5% in 0.5% Acetic Acid at 20° C.) (manufactured by TCI Corporation) in pure water, a precipitate was formed in the solution due to inferior solubility of chitosan, thus failing to perform coating.

TABLE 13

| | Substrate | Moisture content of substrate (%) | Hydrophilic polymer and concentration of solution thereof | Initial pH | pH after heating treatment |
|---|---|---|---|---|---|
| Comparative Example 22 | "1-Day Acuvue TruEye ®" | 46 | 0.2% by mass Sodium alginate | 2.5 | 2.6 |
| Comparative Example 23 | "1-Day Acuvue ®" | 58 | 0.2% by mass Poloxamer 407 | 2.5 | 2.5 |
| Comparative Example 24 | "1-Day Acuvue TruEye ®" | 46 | 0.2% by mass Poloxamer 407 | 2.5 | 2.5 |
| Comparative Example 25 | "1-Day Acuvue ®" | 58 | 0.05% by mass Poly-2-acrylamido-2-methylpropanesulfonic acid | 6.8 | 6.9 |
| Comparative Example 26 | "1-Day Acuvue TruEye ®" | 46 | 0.05% by mass Poly-2-acrylamido-2-methylpropanesulfonic acid | 6.8 | 6.9 |
| Comparative Example 27 | "1-Day Acuvue ®" | 58 | 0.05% by mass 2-Acrylamido-2-methylpropanesulfonic acid/N,Ndimethylacrylamide copolymer | 6.8 | 6.9 |
| Comparative Example 28 | "1-Day Acuvue TruEye ®" | 46 | 0.05% by mass 2-Acrylamido-2-methylpropanesulfonic acid/N,Ndimethylacrylamide copolymer | 6.8 | 6.9 |
| Comparative Example 29 | Reference Example 1 | Less than 1% | 0.1% by mass Acrylic acid/vinylpyrrolidone copolymer Urea: 0.3% by mass | 3.8 | 7.0 |
| Comparative Example 30 | "Medalist ® 1 DAY PLUS" | 59 | 0.1% by mass Acrylic acid/vinylpyrrolidone copolymer Urea: 0.3% by mass | 3.8 | 7.0 |
| Comparative Example 31 | "1-Day Acuvue TruEye ®" | 46 | 0.2% by mass Acrylic acid/N,N-dimethylacrylamide copolymer, Urea: 0.3% by mass | 3.0 | 7.0 |
| Comparative Example 32 | "1-Day Acuvue ®" | 58 | None | None | None |
| Comparative Example 33 | "1-Day Acuvue TruEye ®" | 46 | None | None | None |
| Comparative Example 34 | "Acuvue Oasys ®" | 38 | None | None | None |
| Comparative Example 35 | "AIR OPTIX ® EXAQUA" | 24 | None | None | None |

TABLE 13-continued

|  | Substrate | Moisture content of substrate (%) | Hydrophilic polymer and concentration of solution thereof | Initial pH | pH after heating treatment |
|---|---|---|---|---|---|
| Comparative Example 36 | "Proclear ® 1 Day" | 60 | None | None | None |
| Comparative Example 37 | Reference Example 1 | Less than 1% | 1.2% by mass Polyacrylic acid | 2.6 | No heat treatment |
| Comparative Example 38 | "1-Day Acuvue ®" | 58 | 1.2% by mass Polyacrylic acid | 2.6 | No heating treatment |
| Comparative Example 39 | "1-Day Acuvue TruEye ®" | 46 | 1.2% by mass Polyacrylic acid | 2.6 | No heating treatment |
| Comparative Example 40 | Reference Example 1 | Less than 1% | 0.1% by mass Polyacrylic acid | 3.3 | No heating treatment |
| Comparative Example 41 | "1-Day Acuvue ®" | 58 | 0.1% by mass Polyacrylic acid | 3.3 | No heating treatment |
| Comparative Example 42 | "1-Day Acuvue TruEye ®" | 46 | 0.1% by mass Polyacrylic acid | 3.3 | No heating treatment |
| Comparative Example 43 | Reference Example 1 | Less than 1% | 0.1% by mass Chitosan | *Impossible to perform coating due to inferior solubility | *Impossible to perform coating due to inferior solubility |

TABLE 14

|  | Liquid film retention time (seconds) | Liquid film retention time at 40 minutes after ultrasonic cleaning (seconds) | Lubricity | Moisture content of medical device (%) | Number of hydrophilic polymer layers | Moisture content change rate of substrate and device | Contact angle (°) | Friction coefficient |
|---|---|---|---|---|---|---|---|---|
| Comparative Example 22 | C (5 seconds) | E (0 second) | C | 46 | Impossible to confirm layer | 0 | 46.0 | 0.110 |
| Comparative Example 23 | A (20 seconds) | C (10 seconds) | D | 58 | Impossible to confirm layer | 0 | 52.1 | 0.445 |
| Comparative Example 24 | C (5 seconds) | D (1 second) | C | 46 | Impossible to confirm layer | 0 | 46.8 | 0.105 |
| Comparative Example 25 | A (20 seconds) | C (12 seconds) | D | 58 | Impossible to confirm layer | 0 | 52.0 | 0.450 |
| Comparative Example 26 | D (4 seconds) | D (1 second) | C | 46 | Impossible to confirm layer | 0 | 46.5 | 0.109 |
| Comparative Example 27 | A (20 seconds) | A (20 seconds) | D | 58 | Impossible to confirm layer | 0 | 52.1 | 0.450 |
| Comparative Example 28 | D (3 seconds) | D (1 second) | C | 46 | Impossible to confirm layer | 0 | 46.1 | 0.105 |
| Comparative Example 29 | D (1 second) | D (1 second) | E | Less than 1% | Impossible to confirm layer | 0 | 81.9 | 0.830 |
| Comparative Example 30 | B (15 seconds) | C (10 seconds) | D | 59 | Impossible to confirm layer | 0 | 76.0 | 0.350 |
| Comparative Example 31 | D (2 seconds) | E (0 second) | D | 46 | Impossible to confirm layer | 0 | 47.0 | 0.105 |
| Comparative Example 32 | A (20 seconds) | D (4 seconds) | D | 58 | Impossible to confirm layer | None | 52.1 | 0.434 |
| Comparative Example 33 | D (3 seconds) | D (2 seconds) | C | 46 | Impossible to confirm layer | None | 46.5 | 0.190 |
| Comparative Example 34 | A (20 seconds) | D (4 seconds) | C | 38 | Impossible to confirm layer | None | 50.4 | 0.107 |
| Comparative Example 35 | D (4 seconds) | D (1 second) | D | 24 | Impossible to confirm layer | None | 53.2 | 0.774 |
| Comparative Example 36 | D (4 seconds) | D (4 seconds) | D | 60 | Impossible to confirm layer | None | 55.5 | 0.321 |
| Comparative Example 37 | E (0 second) | E (0 second) | E | Less than 1% | Impossible to confirm layer | 0 | 75.0 | 0.834 |
| Comparative Example 38 | A (83 seconds) | C (10 seconds) | D | 58 | Impossible to confirm layer | 0 | 45.1 | 0.201 |
| Comparative Example 39 | C (14 seconds) | D (4 seconds) | C | 46 | Impossible to confirm layer | 0 | 40.0 | 0.100 |
| Comparative Example 40 | E (0 second) | E (0 second) | E | Less than 1% | Impossible to confirm layer | 0 | 78.5 | 0.833 |
| Comparative Example 41 | A (70 seconds) | A (20 seconds) | D | 58 | Impossible to confirm layer | 0 | 42.0 | 0.210 |
| Comparative Example 42 | B (17 seconds) | C (5 seconds) | C | 46 | Impossible to confirm layer | 0 | 40.3 | 0.102 |

TABLE 14-continued

| | Liquid film retention time (seconds) | Liquid film retention time at 40 minutes after ultrasonic cleaning (seconds) | Lubricity | Moisture content of medical device (%) | Number of hydrophilic polymer layers | Moisture content change rate of substrate and device | Contact angle (°) | Friction coefficient |
|---|---|---|---|---|---|---|---|---|
| Comparative Example 43 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |

TABLE 15

| | Lipid deposition amount | Mucin deposition amount (µg/cm$^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Comparative Example 22 | Deposited in area accounting for 1/5 of entire area | 1.01 | 0.70 | 0.71 | 0.40 |
| Comparative Example 23 | Not deposited | 2.30 | 0.30 | 0.29 | −4.4 |
| Comparative Example 24 | Deposited in area accounting for 1/5 of entire area | 0.99 | 0.70 | 0.71 | 0.40 |
| Comparative Example 25 | Not deposited | 2.20 | 0.30 | 0.29 | −4.4 |
| Comparative Example 26 | Deposited in area accounting for 1/5 of entire area | 0.99 | 0.70 | 0.71 | 0.40 |
| Comparative Example 27 | Not deposited | 2.09 | 0.30 | 0.29 | −4.4 |
| Comparative Example 28 | Deposited in area accounting for 1/5 of entire area | 1.02 | 0.70 | 0.71 | 0.40 |
| Comparative Example 29 | Deposited on entire area | 3.09 | 0.53 | 0.49 | −6.8 |
| Comparative Example 30 | Not deposited | 2.60 | 0.26 | 0.27 | 5.1 |
| Comparative Example 31 | Deposited in area accounting for 1/5 of entire area | 1.04 | 0.70 | 0.71 | 0.40 |
| Comparative Example 32 | Not deposited | 2.10 | 0.30 | None | None |
| Comparative Example 33 | Deposited in area accounting for 1/5 of entire area | 0.94 | 0.70 | None | None |
| Comparative Example 34 | Not deposited | 1.18 | 0.70 | None | None |
| Comparative Example 35 | Not deposited | 2.59 | 1.47 | None | None |
| Comparative Example 36 | Not deposited | 5.07 | 0.39 | None | None |
| Comparative Example 37 | Deposited on entire area | 4.00 | 0.53 | 0.51 | −2.7 |
| Comparative Example 38 | Not deposited | 3.20 | 0.30 | 0.29 | −2.3 |
| Comparative Example 39 | Deposited in area accounting for 1/5 of entire area | 3.50 | 0.70 | 0.71 | 1.3 |
| Comparative Example 40 | Deposited on entire area | 3.89 | 0.53 | 0.53 | 1.3 |
| Comparative Example 41 | Not deposited | 2.99 | 0.30 | 0.29 | −4.2 |
| Comparative Example 42 | Deposited in area accounting for 1/5 of entire area | 3.90 | 0.70 | 0.73 | 3.3 |
| Comparative Example 43 | *Impossible to perform coating due to inferior solubility | *Impossible to perform coating due to inferior solubility | 0.53 | *Impossible to perform coating due to inferior solubility | *Impossible to perform coating due to inferior solubility |

TABLE 16

| | Size of substrate (mm) | Size of medical device (mm) | Size change rate due to formation of hydrophilic polymer layer (%) | Thickness of hydrophilic polymer layer of front curve surface - dry state - (nm) | Thickness of hydrophilic polymer layer of base curve surface - dry state - (nm) | Average thickness difference (%) | Thickness of hydrophilic polymer layer of front curve surface - frozen state - (nm) |
|---|---|---|---|---|---|---|---|
| Comparative Example 22 | 14.20 | 14.20 | 0.0 | 0 | 0 | 0 | 0 |
| Comparative Example 23 | 14.20 | 14.10 | −0.7 | 0 | 0 | 0 | 0 |
| Comparative Example 24 | 14.20 | 14.20 | 0.0 | 0 | 0 | 0 | 0 |
| Comparative Example 25 | 14.20 | 14.10 | −0.7 | 0 | 0 | 0 | 0 |
| Comparative Example 26 | 14.20 | 14.20 | 0.0 | 0 | 0 | 0 | 0 |
| Comparative Example 27 | 14.20 | 14.10 | −0.7 | 0 | 0 | 0 | 0 |
| Comparative Example 28 | 14.20 | 14.20 | 0.0 | 0 | 0 | 0 | 0 |
| Comparative Example 29 | 14.00 | 14.00 | 0.0 | 0 | 0 | 0 | 0 |
| Comparative Example 30 | 14.00 | 14.00 | 0.0 | 0 | 0 | 0 | 0 |
| Comparative Example 31 | 14.20 | 14.10 | −0.7 | 0 | 0 | 0 | 0 |
| Comparative Example 32 | 14.20 | None | None | 0 | 0 | 0 | 0 |
| Comparative Example 33 | 14.20 | None | None | 0 | 0 | 0 | 0 |
| Comparative Example 34 | 14.00 | None | None | 0 | 0 | 0 | 0 |
| Comparative Example 35 | 13.80 | None | None | 0 | 0 | 0 | 0 |
| Comparative Example 36 | 14.20 | None | None | 0 | 0 | 0 | 0 |
| Comparative Example 37 | 14.00 | 14.00 | 0.0 | 0 | 0 | 0 | 0 |
| Comparative Example 38 | 14.20 | 14.10 | −0.7 | 0 | 0 | 0 | 0 |
| Comparative Example 39 | 14.20 | 14.20 | 0.0 | 0 | 0 | 0 | 0 |
| Comparative Example 40 | 14.00 | 14.00 | 0.0 | 0 | 0 | 0 | 0 |
| Comparative Example 41 | 14.20 | 14.10 | −0.7 | 0 | 0 | 0 | 0 |
| Comparative Example 42 | 14.20 | 14.15 | −0.4 | 0 | 0 | 0 | 0 |
| Comparative Example 43 | 14.00 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |

Comparative Example 44

The molded body obtained in Reference Example 1 was used as a substrate. The substrate was immersed in a phosphate buffer solution containing 0.18% by mass of polyacrylic acid (number ratio of basic group/acidic group: 0, "Sokalan PA110S", Mw 250,000, manufactured by BASF Corporation) and 0.02% by mass of an acrylic acid/N,N-dimethylacrylamide copolymer (copolymerization ratio: 1/9, Mw 800,000, manufactured by Osaka Organic Chemical Industry Ltd.), followed by heating in an autoclave at 121° C. for 30 minutes. The results obtained by evaluation of the molded body thus obtained (a hydrophilic polymer layer was not confirmed) using the above method are shown in Tables 17 to 20.

Comparative Example 45

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in a phosphate buffer solution containing 0.18% by mass of polyacrylic acid (number ratio of basic group/acidic group: 0, "Sokalan PA110S", Mw 250,000, manufactured by BASF Corporation) and 0.02% by mass of an acrylic acid/N,N-dimethylacrylamide copolymer (number ratio of basic group/acidic group: 0, copolymerization ratio: 1/9, Mw 800,000, manufactured by Osaka Organic Chemical Industry Ltd.), followed by heating in an autoclave at 121° C. for 30 minutes. The results obtained by evaluation of the molded body thus obtained (a hydrophilic polymer layer was not confirmed) using the above method are shown in Tables 17 to 20.

Comparative Example 46

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a phosphate buffer solution containing 0.18% by mass of polyacrylic acid (number ratio of basic group/acidic group: 0, "Sokalan PA110S", Mw 250,000, manufactured by BASF Corporation) and 0.02% by mass of an acrylic acid/N,N-dimethylacrylamide copolymer (number ratio of basic group/acidic group: 0, copolymerization ratio: 1/9, Mw 800,000, manufactured by Osaka Organic Chemical Industry Ltd.), followed by heating in an autoclave at 121° C. for 30 minutes. The results obtained by evaluation of the molded body thus obtained (a hydrophilic polymer layer was not confirmed) using the above method are shown in Tables 17 to 20.

Comparative Example 47

The molded body obtained in Reference Example 1 was used as a substrate. The substrate was immersed in a solution prepared by dissolving polyacrylic acid (number ratio of basic group/acidic group: 0, "Sokalan PA110S", Mw 250,000, manufactured by BASF Corporation) dissolved in pure water to the concentration of 1.2% by mass at room temperature for 30 minutes. Thereafter, the substrate was rinsed lightly with pure water in a beaker. The molded body was transferred to a beaker containing fresh pure water and then cleaned in an ultrasonic cleaner (for 30 seconds). Furthermore, the molded body was rinsed lightly in a beaker containing fresh pure water. Next, using each of a solution prepared by dissolving polyethyleneimine (number ratio of basic group/acidic group: 0, Mw: 750,000, manufactured by Junsei Chemical Co., Ltd.) in pure water to the concentration of 1% by mass and a solution prepared by dissolving an acrylic acid/N,N-dimethylacrylamide copolymer (number ratio of basic group/acidic group: 0, copolymerization ratio: 1/9, Mw 800,000, manufactured by Osaka Organic Chemical Industry Ltd.) in pure water to the concentration of 0.1% by mass, the same operation was repeated in this order. After completion of the coating operation, the molded body was immersed in a phosphate buffer solution, followed by heating in an autoclave at 121° C. for 30 minutes. The results obtained by evaluation of the molded body thus obtained (number ratio of basic group/acidic group of hydrophilic polymer layer: 0.5) using the above method are shown in Tables 17 to 20.

Comparative Example 48

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in a solution prepared by dissolving polyacrylic acid ("Sokalan PA110S", Mw 250,000, manufactured by BASF Corporation) dissolved in pure water to the concentration of 1.2% by mass at room temperature for 30 minutes. Thereafter, the substrate was rinsed lightly with pure water in a beaker. The molded body was transferred to a beaker containing fresh pure water and then cleaned in an ultrasonic cleaner (for 30 seconds). Furthermore, the molded body was rinsed lightly in a beaker containing fresh pure water. Next, using each of a solution prepared by dissolving polyethyleneimine (Mw: 750,000, manufactured by Junsei Chemical Co., Ltd.) in pure water to the concentration of 1% by mass and a solution prepared by dissolving an acrylic acid/N,N-dimethylacrylamide copolymer (copolymerization ratio: 1/9, Mw 800,000, manufactured by Osaka Organic Chemical Industry Ltd.) in pure water to the concentration of 0.1% by mass, the same operation was repeated in this order. After completion of the coating operation, the molded body was immersed in a phosphate buffer solution, followed by heating in an autoclave at 121° C. for 30 minutes. The results obtained by evaluation of the molded body thus obtained (number ratio of basic group/acidic group of hydrophilic polymer layer: 0.5) using the above method are shown in Tables 17 to 20.

Comparative Example 49

A commercially available hydrogel lens containing 2-hydroxyethyl methacrylate as a main component "1-Day Acuvue (registered trademark)" (etafilcon A, manufactured by Johnson & Johnson) was used as a substrate. The substrate was immersed in a solution prepared by dissolving polyacrylic acid ("Sokalan PA110S", Mw 250,000, manufactured by BASF Corporation) in pure water to the concentration of 1.2% by mass at room temperature for 30 minutes. Thereafter, the substrate was rinsed lightly with pure water in a beaker. The molded body was transferred to a beaker containing fresh pure water and then cleaned in an ultrasonic cleaner (for 30 seconds). Furthermore, the molded body was rinsed lightly in a beaker containing fresh pure water. Next, using each of a solution prepared by dissolving polyethyleneimine (Mw: 750,000, manufactured by Junsei Chemical Co., Ltd.) in pure water to the concentration of 1% by mass and a solution prepared by dissolving an acrylic acid/N,N-dimethylacrylamide copolymer (copolymerization ratio: 1/9, Mw 800,000, manufactured by Osaka Organic Chemical Industry Ltd.) in pure water to the concentration of 0.1% by mass, the same operation was repeated in this order. After completion of the coating operation, the molded body was greatly deformed, thus failing to form a lens shape, so that the molded body could not be used for evaluation.

Comparative Example 50

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. The substrate was immersed in an aqueous solution containing 0.1% by mass of an acrylic acid/N,N-dimethylacrylamide copolymer (number ratio of basic group/acidic group: 0, molar ratio in copolymerization: 1/9, Mw: 200,000, manufactured by Osaka Organic Chemical Industry Ltd.) in pure water, which has the pH of 3.5 adjusted with sulfuric acid, and then subjected to ultrasonic cleaning (Model US-IR, manufactured by AS ONE Corporation) at a temperature between room temperature and about 40° C. for 2 hours. The molded body thus obtained was washed while immersing in pure water for 30 seconds and, after replacing by a fresh phosphate buffer solution, the molded body was further heated in an autoclave at 121° C. for 30 minutes. The results obtained by evaluation of the molded body thus obtained (a hydrophilic polymer layer was not confirmed) using the above method are shown in Tables 17 to 20.

Comparative Example 51

The molded body obtained in Reference Example 1 was used as a substrate. The substrate was immersed in an aqueous solution containing 0.1% by mass of an acrylic acid/N,N-dimethylacrylamide copolymer (number ratio of basic group/acidic group: 0, molar ratio in copolymerization: 1/9, Mw: 200,000, manufactured by Osaka Organic Chemical Industry Ltd.) in pure water, which has the pH of 3.5 adjusted with sulfuric acid, and then subjected to ultrasonic cleaning (Model US-IR, manufactured by AS ONE Corporation) at a temperature between room temperature and about 40° C. for 2 hours. The molded body thus obtained was washed while immersing in pure water for 30 seconds and, after replacing by a fresh phosphate buffer solution, the molded body was further heated in an autoclave at 121° C. for 30 minutes. The results obtained by evaluation of the molded body thus obtained (a hydrophilic polymer layer was not confirmed) using the above method are shown in Tables 17 to 20.

Comparative Example 52

A commercially available hydrogel lens "Proclea 1 Day" (manufactured by Cooper Vision) containing 2-hydroxyethyl methacrylate copolymerized with an MPC monomer (2-methacryloyloxyethyl phosphorylcholine) as a main component was used as a substrate. The substrate was immersed in an aqueous solution containing 0.1% by mass of an acrylic acid/N,N-dimethylacrylamide copolymer (number ratio of basic group/acidic group: 0, molar ratio in copolymerization: 1/9, Mw: 200,000, manufactured by Osaka Organic Chemical Industry Ltd.) in pure water, which has the pH of 3.5 adjusted with sulfuric acid, and then subjected to ultrasonic cleaning (Model US-IR, manufactured by AS ONE Corporation) at a temperature between room temperature and about 40° C. for 2 hours. The molded body thus obtained was washed while immersing in pure water for 30 seconds and, after replacing by a fresh phosphate buffer solution, the molded body was further heated in an autoclave at 121° C. for 30 minutes. The results obtained by evaluation of the molded body thus obtained (a hydrophilic polymer layer was not confirmed) using the above method are shown in Tables 17 to 20.

Comparative Example 53

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in an aqueous solution containing 0.1% by mass of an acrylic acid/N,N-dimethylacrylamide copolymer (number ratio of basic group/acidic group: 0, molar ratio in copolymerization: 1/9, Mw: 200,000, manufactured by Osaka Organic Chemical Industry Ltd.) in pure water, which has the pH of 3.5 adjusted with sulfuric acid, followed by heating in an autoclave at 121° C. for 30 minutes. The molded body thus obtained was washed while immersing in pure water for 30 seconds and, after replacing by a fresh phosphate buffer solution, the molded body was further heated in an autoclave at 121° C. for 30 minutes. The results obtained by evaluation of the molded body thus obtained (a hydrophilic polymer layer was not confirmed) using the above method are shown in Tables 17 to 20.

Comparative Example 54

The molded body obtained in Reference Example 1 was used as a substrate. The substrate was immersed in an aqueous solution containing 0.1% by mass of an acrylic acid/N,N-dimethylacrylamide copolymer (number ratio of basic group/acidic group: 0, molar ratio in copolymerization: 1/9, Mw: 200,000, manufactured by Osaka Organic Chemical Industry Ltd.) in pure water, which has the pH of 3.5 adjusted with sulfuric acid, followed by heating in an autoclave at 121° C. for 30 minutes. The molded body thus obtained was washed while immersing in pure water for 30 seconds and, after replacing by a fresh phosphate buffer solution, the molded body was further heated in an autoclave at 121° C. for 30 minutes. The results obtained by evaluation of the molded body thus obtained (a hydrophilic polymer layer was not confirmed) using the above method are shown in Tables 17 to 20.

Comparative Example 55

A commercially available silicone hydrogel lens containing polyvinylpyrrolidone and silicone as main components "Acuvue Oasys (registered trademark)" (manufactured by Johnson & Johnson) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in pure water was adjusted to pH 1.9 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing the phosphate buffer solution by a fresh phosphate buffer solution, the molded body was further heated in the autoclave at 121° C. for 30 minutes. Since the molded body thus obtained has a thick polymer layer, refraction of light is disturbed, and when the character on the opposite side of the lens is seen through the lens in the air, the opposite character is blurred, thus failing to recognize, i.e., optical performance required for the lens was remarkably insufficient. The results obtained by evaluation of the molded body thus obtained using the above method are shown in Tables 17 to 20.

Comparative Example 56

A commercially available hydrogel lens containing 2-hydroxyethyl methacrylate as a main component "1-Day Acuvue (registered trademark)" (etafilcon A, manufactured by Johnson & Johnson) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in pure water was adjusted to pH 1.9 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing the phosphate buffer solution by a fresh phosphate buffer solution, the molded body was further heated in the autoclave at 121° C. for 30 minutes. Since the molded body thus obtained has a thick polymer layer, refraction of light is disturbed, and when the character on the opposite side of the lens is seen through the lens in the air, the opposite character is blurred, thus failing to recognize, i.e., optical performance required for the lens was remarkably insufficient. The results obtained by evaluation of the molded body thus obtained using the above method are shown in Tables 17 to 20.

Comparative Example 57

The molded body obtained in Reference Example 1 was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) in pure water was adjusted to pH 1.9 with sulfuric acid. The substrate was immersed in the solution, followed by heating in an autoclave at 121° C. for 30 minutes. The molded body thus obtained was washed with a phosphate buffer solution while shaking at 250 rpm for 10 seconds and, after replacing the phosphate buffer solution by a fresh phosphate buffer solution, the molded body was further heated in the autoclave at 121° C. for 30 minutes. Since the molded body thus obtained has a thick polymer layer, refraction of light is disturbed, and when the character on the opposite side of the lens is seen through the lens in the air, the opposite character is blurred, thus failing to recognize, i.e., optical performance required for the lens was remarkably insufficient. The results obtained by evaluation of the molded body thus obtained using the above method are shown in Tables 17 to 20.

Comparative Example 58

A commercially available silicone hydrogel lens containing silicone as a main component "MyDay (registered trademark)" (stenfilcon A, manufactured by CooperVision Inc.) was used as a substrate. After making a trial of immersing the substrate in an aqueous solution containing 0.19% by mass of an acrylic acid/acrylamide copolymer (number ratio of basic group/acidic group: 0, molar ratio in copolymerization: 6/4, Mw: 200,000, manufactured by oneself) in a phosphate buffer solution, which has the pH of 3.2 adjusted with citric acid, a white precipitate was formed in the solution adjusted to pH 3.2, thus failing to perform coating.

Comparative Example 59

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/acrylamide copolymer (number ratio of basic group/acidic group: 0, molar ratio in copolymerization: 7/93, Mw: 200,000, manufactured by oneself) in a phosphate buffer solution was adjusted to pH 3.2 with citric acid. The substrate was immersed in the solution, followed by heating in an autoclave at 121° C. for 30 minutes. The molded body thus obtained was washed with a phosphate buffer solution while immersing for 30 seconds and, after replacing the phosphate buffer solution by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 17 to 20.

Comparative Example 60

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/acrylamide copolymer (number ratio of basic group/acidic group: 0, molar ratio in copolymerization: 1/9, Mw: 200,000, manufactured by oneself) in a phosphate buffer solution was adjusted to pH 3.2 with citric acid. The substrate was immersed in the solution, followed by heating in an autoclave at 121° C. for 30 minutes. The molded body thus obtained was washed with a phosphate buffer solution while immersing for 30 seconds and, after replacing the phosphate buffer solution by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 17 to 20.

Comparative Example 61

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/acrylamide copolymer (number ratio of basic group/acidic group: 0, molar ratio in copolymerization: 3/7, Mw: 200,000, manufactured by oneself) in a phosphate buffer solution was adjusted to pH 3.2 with citric acid. The substrate was immersed in the solution, followed by heating in an autoclave at 121° C. for 30 minutes. The molded body thus obtained was washed with a phosphate buffer solution while immersing for 30 seconds and, after replacing the phosphate buffer solution by a fresh phosphate buffer solution, the molded body was further heated in the autoclave at 121° C. for 30 minutes. The results obtained by evaluation of the molded body thus obtained (a hydrophilic polymer layer was not confirmed) using the above method are shown in Tables 17 to 20.

Comparative Example 62

The results obtained by evaluation of a commercially available silicone hydrogel lens containing silicone as a main component "MyDay (registered trademark)" (stenfilcon A, manufactured by CooperVision Inc.) using the above method are shown in Tables 17 to 20.

TABLE 17

| | Substrate | Moisture content of substrate (%) | Hydrophilic polymer and concentration of solution thereof | Initial pH | pH after heating treatment |
|---|---|---|---|---|---|
| Comparative Example 44 | Reference Example 1 | Less than 1% | 0.18% by mass Polyacrylic acid, 0.02% by mass Acrylic acid/N,N-dimethylacrylamide copolymer | 4.5 | 4.6 |
| Comparative Example 45 | "1-Day Acuvue TruEye ®" | 46 | | 4.5 | 4.6 |
| Comparative Example 46 | "1-Day Acuvue ®" | 58 | | 4.5 | 4.6 |
| Comparative Example 47 | Reference Example 1 | Less than 1% | 0.12% by mass Polyacrylic acid, 1.0% by mass | None | None |

TABLE 17-continued

| | Substrate | Moisture content of substrate (%) | Hydrophilic polymer and concentration of solution thereof | Initial pH | pH after heating treatment |
|---|---|---|---|---|---|
| Comparative Example 48 | "1-Day Acuvue TruEye ®" | 46 | Polyethyleneimine, 0.1% by mass Acrylic acid/N,N-dimethylacrylamide copolymer | None | None |
| Comparative Example 49 | "1-Day Acuvue ®" | 58 | | None | None |
| Comparative Example 50 | "1-Day Acuvue TruEye ®" | 46 | 0.1% by mass Acrylic acid/N,N-dimethylacrylamide copolymer | None | None |
| Comparative Example 51 | Reference Example 1 | Less than 1% | | 3.5 | None |
| Comparative Example 52 | "Proclear ® 1 Day" | 60 | | 3.5 | None |
| Comparative Example 53 | "1-Day Acuvue TruEye ®" | 46 | 0.1% by mass Acrylic acid/N,N-dimethylacrylamide copolymer | 3.5 | 5.9 |
| Comparative Example 54 | Reference Example 1 | Less than 1% | | 3.5 | 5.9 |
| Comparative Example 55 | "Acuvue Oasys ®" | 38 | 0.2% by mass Acrylic acid/N,N-dimethylacrylamide copolymer | 1.9 | 2.3 |
| Comparative Example 56 | "1-Day Acuvue ®" | 58 | | 1.9 | 2.3 |
| Comparative Example 57 | Reference Example 1 | Less than 1% | | 1.9 | 2.6 |
| Comparative Example 58 | "MyDay ®" | 54 | 0.19% by mass Acrylic acid/acrylamide copolymer | *Impossible to perform coating due to formation of white precipitate in solution | *Impossible to perform coating due to formation of white precipitate in solution |
| Comparative Example 59 | "MyDay ®" | 54 | 0.19% by mass Acrylic acid/acrylamide copolymer | 3.2 | 3.3 |
| Comparative Example 60 | "MyDay ®" | 54 | 0.19% by mass Acrylic acid/acrylamide copolymer | 3.2 | 3.3 |
| Comparative Example 61 | "MyDay ®" | 54 | 0.19% by mass Acrylic acid/acrylamide copolymer | 3.2 | 3.4 |
| Comparative Example 62 | "MyDay ®" | 54 | None | None | None |

TABLE 18

| | Liquid film retention time (seconds) | Liquid film retention time at 40 after minutes of ultrasonic cleaning (seconds) | Lubricity | Moisture content of medical device (%) | Number of hydrophilic polymer layers |
|---|---|---|---|---|---|
| Comparative Example 44 | C (5 seconds) | E (0 second) | E | Less than 1% | Impossible to confirm layer |
| Comparative Example 45 | D (2 second) | E (0 second) | C | 46 | Impossible to confirm layer |
| Comparative Example 46 | A (20 seconds) | C (7 seconds) | D | 58 | Impossible to confirm layer |
| Comparative Example 47 | C (12 seconds) | D (3 seconds) | C | Less than 1% | Two layers |
| Comparative Example 48 | A (50 seconds) | D (2 seconds) | C | 46 | Two layers |
| Comparative Example 49 | *Impossible to perform measurement due to lens deformation | *Impossible to perform measurement due to lens deformation | *Impossible to perform measurement due to lens deformation | *Impossible to perform measurement due to lens deformation | *Impossible to perform measurement due to lens deformation |
| Comparative Example 50 | D (2 seconds) | E (0 second) | C | 46 | Impossible to confirm layer |
| Comparative Example 51 | E (0 second) | E (0 second) | E | Less than 1% | Impossible to confirm layer |
| Comparative Example 52 | D (4 seconds) | D (4 seconds) | D | 60 | Impossible to confirm layer |
| Comparative Example 53 | D (2 seconds) | E (0 second) | C | 46 | Impossible to confirm layer |
| Comparative Example 54 | D (1 second) | E (0 second) | E | Less than 1% | Impossible to confirm layer |

TABLE 18-continued

| | | | | | |
|---|---|---|---|---|---|
| Comparative Example 55 | A (120 seconds or more) | A (120 seconds or more) | A | 63 | Coating polymer was separated into two layers (one layer of which was mixed with substrate) |
| Comparative Example 56 | A (120 seconds or more) | A (120 seconds or more) | A | 73 | Coating polymer was separated into two layers (one layer of which was mixed with substrate) |
| Comparative Example 57 | A (120 seconds or more) | A (120 seconds or more) | A | 76 | Coating polymer was separated into two layers (one layer of which was mixed with substrate), Layer which is not mixed with substrate was separated into two layers |
| Comparative Example 58 | *Impossible to perform coating due to formation of white precipitate in solution | *Impossible to perform coating due to formation of white precipitate in solution | *Impossible to perform coating due to formation of white precipitate in solution | *Impossible to perform coating due to formation of white precipitate in solution | *Impossible to perform coating due to formation of white precipitate in solution |
| Comparative Example 59 | D (3 seconds) | D (1 second) | C | 54 | Impossible to confirm layer |
| Comparative Example 60 | D (4 seconds) | D (1 second) | C | 54 | Impossible to confirm layer |
| Comparative Example 61 | D (3 seconds) | D (2 seconds) | C | 54 | Impossible to confirm layer |
| Comparative Example 62 | D (2 seconds) | D (2 seconds) | C | None | Impossible to confirm layer |

| | Moisture content change rate of substrate and device | Contact angle (°) | Friction coefficient |
|---|---|---|---|
| Comparative Example 44 | 0 | 81.9 | 0.830 |
| Comparative Example 45 | 0 | 46.0 | 0.110 |
| Comparative Example 46 | 0 | 52.0 | 0.450 |
| Comparative Example 47 | 0 | 56.0 | 0.200 |
| Comparative Example 48 | 0 | 45.5 | 0.100 |
| Comparative Example 49 | *Impossible to perform measurement due to lens deformation | *Impossible to perform measurement due to lens deformation | *Impossible to perform measurement due to lens deformation |
| Comparative Example 50 | 0 | 46.0 | 0.140 |
| Comparative Example 51 | 0 | 82.0 | 0.810 |
| Comparative Example 52 | 0 | 55.9 | 0.340 |
| Comparative Example 53 | 0 | 46.0 | 0.140 |
| Comparative Example 54 | 0 | 81.0 | 0.820 |
| Comparative Example 55 | 25 | 39.0 | 0.006 |
| Comparative Example 56 | 15 | 38.0 | 0.001 |
| Comparative Example 57 | 76 | 32.6 | 0.002 |
| Comparative Example 58 | *Impossible to perform coating due to formation of white precipitate in solution | *Impossible to perform coating due to formation of white precipitate in solution | *Impossible to perform coating due to formation of white precipitate in solution |

TABLE 18-continued

|  |  |  |  |
|---|---|---|---|
| Comparative Example 59 | 0 | 47.0 | 0.277 |
| Comparative Example 60 | 0 | 47.2 | 0.218 |
| Comparative Example 61 | 0 | 48.8 | 0.377 |
| Comparative Example 62 | None | 47.8 | 0.235 |

TABLE 19

|  | Lipid deposition amount | Mucin deposition amount (μg/cm$^2$) | Tensile elastic modulus of substrate (MPa) | Tensile elastic modulus of medical device (MPa) | Tensile elastic modulus change rate due to formation of hydrophilic polymer layer (%) |
|---|---|---|---|---|---|
| Comparative Example 44 | Deposited on entire area | 3.09 | 0.53 | 0.49 | −6.8 |
| Comparative Example 45 | Deposited in area accounting for ⅓ of entire area | 1.01 | 0.70 | 0.71 | 0.40 |
| Comparative Example 46 | Not deposited | 2.20 | 0.30 | 0.29 | −4.4 |
| Comparative Example 47 | Not deposited | 2.90 | 0.53 | 0.49 | −6.8 |
| Comparative Example 48 | Not deposited | 1.50 | 0.70 | 0.71 | 0.40 |
| Comparative Example 49 | *Impossible to perform measurement due to lens deformation | *Impossible to perform measurement due to lens deformation | *Impossible to perform measurement due to lens deformation | *Impossible to perform measurement due to lens deformation | *Impossible to perform measurement due to lens deformation |
| Comparative Example 50 | Deposited in area accounting for ⅓ of entire area | 1.10 | 0.70 | 0.71 | 1.3 |
| Comparative Example 51 | Deposited on entire area | 3.16 | 0.53 | 0.49 | −6.7 |
| Comparative Example 52 | Not deposited | 5.18 | 0.39 | 0.40 | 2.0 |
| Comparative Example 53 | Deposited in area accounting for ⅓ of entire area | 1.15 | 0.70 | 0.71 | 0.3 |
| Comparative Example 54 | Not deposited | 3.20 | 0.53 | 0.48 | −8.0 |
| Comparative Example 55 | Not deposited | 25.0 | 0.70 | *Impossible to perform coating due to inferior solubility | *Impossible to perform coating due to inferior solubility |
| Comparative Example 56 | Not deposited | 26.3 | 0.30 | *Impossible to perform coating due to inferior solubility | *Impossible to perform coating due to inferior solubility |
| Comparative Example 57 | Not deposited | 28.1 | 0.53 | *Impossible to perform coating due to inferior solubility | *Impossible to perform coating due to inferior solubility |
| Comparative Example 58 | *Impossible to perform coating due to formation of white precipitate in solution | *Impossible to perform coating due to formation of white precipitate in solution | 0.61 | *Impossible to perform coating due to formation of white precipitate in solution | *Impossible to perform coating due to formation of white precipitate in solution |
| Comparative Example 59 | Deposited in area accounting for ⅓ of entire area | 2.60 | 0.61 | 0.61 | 0.2 |
| Comparative Example 60 | Deposited in area accounting for ⅓ of entire area | 2.49 | 0.61 | 0.61 | 0.2 |
| Comparative Example 61 | Deposited in area accounting for ⅓ of entire area | 2.60 | 0.61 | 0.61 | 0.2 |
| Comparative Example 62 | Deposited in area accounting for ⅓ of entire area | 2.53 | 0.61 | None | None |

TABLE 20

| | Size of substrate (mm) | Size of medical device (mm) | Size change rate due to formation of hydrophilic polymer layer (%) | Thickness of hydrophilic polymer layer of front curve surface - dry state - (nm) | Thickness of hydrophilic polymer layer of base curve surface - dry state - (nm) | Average thickness difference (%) | Thickness of hydrophilic polymer layer of front curve surface - frozen state - (nm) |
|---|---|---|---|---|---|---|---|
| Comparative Example 44 | 14.00 | 14.00 | 0.0 | 0 | 0 | 0 | 0 |
| Comparative Example 45 | 14.20 | 14.20 | 0.0 | 0 | 0 | 0 | 0 |
| Comparative Example 46 | 14.20 | 14.10 | −0.7 | 0 | 0 | 0 | 0 |
| Comparative Example 47 | 14.00 | 14.00 | 0.0 | 14.5 | 14.0 | 4 | 30 to 35 |
| Comparative Example 48 | 14.20 | 14.20 | 0.0 | 11.9 | 12.5 | 5 | 29 to 34 |
| Comparative Example 49 | *Impossible to perform measurement due to lens deformation | *Impossible to perform measurement due to lens deformation | *Impossible to perform measurement due to lens deformation | *Impossible to perform measurement due to lens deformation | *Impossible to perform measurement due to lens deformation | *Impossible to perform measurement due to lens deformation | *Impossible to perform measurement due to lens deformation |
| Comparative Example 50 | 14.20 | 14.20 | 0.0 | 0 | 0 | 0 | 0 |
| Comparative Example 51 | 14.00 | 14.00 | 0.0 | 0 | 0 | 0 | 0 |
| Comparative Example 52 | 14.20 | 14.20 | 0.00 | 0 | 0 | 0 | 0 |
| Comparative Example 53 | 14.20 | 14.20 | 0.0 | 0 | 0 | 0 | 0 |
| Comparative Example 54 | 14.00 | 14.00 | 0.0 | 0 | 0 | 0 | 0 |
| Comparative Example 55 | 14.00 | 16.8 | 20 | 265 | 225 | 17.8 | 310 to 400 |
| Comparative Example 56 | 14.20 | 17.1 | 20 | 1008 | 870 | 15.9 | 2010 to 2670 |
| Comparative Example 57 | 14.00 | 16.5 | 18 | 455 | 405 | 12.3 | 610 to 740 |
| Comparative Example 58 | 14.20 | *Impossible to perform coating due to formation of white precipitate in solution | *Impossible to perform coating due to formation of white precipitate in solution | *Impossible to perform coating due to formation of white precipitate in solution | *Impossible to perform coating due to formation of white precipitate in solution | *Impossible to perform coating due to formation of white precipitate in solution | *Impossible to perform coating due to formation of white precipitate in solution |
| Comparative Example 59 | 14.20 | 14.19 | −0.1 | 0 | 0 | 0 | 0 |
| Comparative Example 60 | 14.20 | 14.20 | 0.0 | 0 | 0 | 0 | 0 |
| Comparative Example 61 | 14.20 | 14.20 | 0.0 | 0 | 0 | 0 | 0 |
| Comparative Example 62 | 14.20 | None | None | 0 | 0 | 0 | 0 |

The invention claimed is:

1. A medical device comprising a substrate and a hydrophilic polymer layer formed on at least a part of the substrate, which satisfies the following conditions (a) to (d):
   (a) a polymer constituting the hydrophilic polymer layer is a hydrophilic polymer having an acidic group;
   (b) the hydrophilic polymer layer has a thickness of 1 nm or more and less than 100 nm;
   (c) a number ratio of basic group/acidic group of the hydrophilic polymer layer is 0.05 or less; and
   (d) a liquid film retention time at 40 minutes after ultrasonic cleaning in a phosphate buffer solution is 15 seconds or more.

2. The medical device according to claim 1, wherein at least a part of the hydrophilic polymer layer exists in a state of being mixed with the substrate.

3. The medical device according to claim 1, wherein the hydrophilic polymer further has an amide group.

4. The medical device according to claim 1, wherein the substrate contains one or more materials selected from a hydrogel, a silicone hydrogel, a low water content soft material and a low water content hard material.

5. The medical device according to claim 4, wherein the hydrogel is a hydrogel selected from the group consisting of tefilcon, tetrafilcon, helfilcon, mafilcon, polymacon, hioxifilcon, alfafilcon, omafilcon, hioxifilcon, nelfilcon, nesofilcon, hilafilcon, acofilcon, deltafilcon, etafilcon, focofilcon, ocufilcon, phemfilcon, methafilcon, and vilfilcon.

6. The medical device according to claim 4, wherein the silicone hydrogel is a silicone hydrogel selected from the group consisting of lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon.

7. The medical device according to claim 4, wherein the low water content soft material is a material having a silicon atom.

8. The medical device according to claim 4, wherein the low water content hard material is a material having a silicon atom.

9. The medical device according to claim 4, wherein the low water content hard material is polymethyl methacrylate.

10. The medical device according to claim 4, wherein the low water content hard material is a material selected from the group consisting of neofocon, pasifocon, telefocon, silafocon, paflufocon, petrafocon, and fluorofocon.

11. The medical device according to claim 1, which is an ophthalmic lens, a dermal covering material, a wound dressing material, a skin protection material, a skin medicine carrier, an infusion tube, a gas delivery tube, a drain tube, a blood circuit, a covering tube, a catheter, a stent, a sheath biosensor chip, or an endoscopic covering material.

12. The medical device according to claim 11, which is a contact lens satisfying the following condition (e):
   (e) an average thickness of a hydrophilic polymer layer on a front curve surface and an average thickness of a hydrophilic polymer layer on a base curve surface has a thickness difference of more than 20%.

13. The medical device according to claim 11, wherein the medical device is a contact lens.

14. A method for manufacturing the medical device according to claim 1, the method comprising:
   a step of disposing the substrate in a solution having an initial pH of 2.0 or higher and 6.0 or lower and heating the solution,
   wherein the solution contains the hydrophilic polymer and an acid.

15. The method for manufacturing the medical device according to claim 14, wherein the acid is an organic acid containing one or more acids selected from acetic acid, citric acid, formic acid, ascorbic acid, trifluoromethanesulfonic acid, methanesulfonic acid, propionic acid, butyric acid, glycolic acid, lactic acid, and malic acid.

16. The method for manufacturing the medical device according to claim 14, wherein the step of heating the solution is performed using an autoclave.

* * * * *